(12) United States Patent
Lo et al.

(10) Patent No.: US 9,977,875 B2
(45) Date of Patent: May 22, 2018

(54) SYSTEMS AND METHODS OF MANAGING TREATMENT OF A CHRONIC CONDITION BY SYMPTOM TRACKING

(71) Applicant: CORCEPT THERAPEUTICS, INC., Menlo Park, CA (US)

(72) Inventors: Steven Lo, Menlo Park, CA (US); David Penake, Menlo Park, CA (US); John Lyons, Menlo Park, CA (US); Lisa Saginian, Menlo Park, CA (US)

(73) Assignee: CORCEPT THERAPEUTICS, INC., Menlo Park, CA (US)

( * ) Notice: Subject to any disclaimer, the term of this patent is extended or adjusted under 35 U.S.C. 154(b) by 0 days. days.

(21) Appl. No.: 14/715,311

(22) Filed: May 18, 2015

(65) Prior Publication Data

US 2015/0332020 A1    Nov. 19, 2015

Related U.S. Application Data

(60) Provisional application No. 61/994,815, filed on May 16, 2014.

(51) Int. Cl.
| | |
|---|---|
| *G01N 33/48* | (2006.01) |
| *G06F 19/00* | (2018.01) |
| *A61K 31/567* | (2006.01) |
| *G01N 33/49* | (2006.01) |
| *G06G 7/58* | (2006.01) |

(52) U.S. Cl.
CPC ........ *G06F 19/3487* (2013.01); *A61K 31/567* (2013.01); *G01N 33/492* (2013.01); *G16H 15/00* (2018.01)

(58) Field of Classification Search
CPC .......... G06F 19/18; G06F 19/22; G06F 19/24; G01N 33/582
See application file for complete search history.

(56) References Cited

U.S. PATENT DOCUMENTS

| | | |
|---|---|---|
| 2005/0283385 A1 | 12/2005 | Hunkeler et al. |
| 2006/0036619 A1 | 2/2006 | Fuerst et al. |
| 2010/0169409 A1 | 7/2010 | Fallon et al. |
| 2011/0224179 A1 | 9/2011 | Newell-Price et al. |
| 2013/0131030 A1 | 5/2013 | Belanoff et al. |
| 2013/0144676 A1 | 6/2013 | O'Sullivan et al. |
| 2015/0088540 A1 | 3/2015 | Lo et al. |

FOREIGN PATENT DOCUMENTS

| | | |
|---|---|---|
| CN | 103690149 A | 4/2014 |
| WO | 20150176062 A3 | 12/2015 |

OTHER PUBLICATIONS

PCT/US2015/031408, "International Preliminary Report on Patentability", dated Dec. 1, 2016, 8 pages.
Cushing syndrome definition, Mayo Clinic, retrieved online Jul. 13, 2015, at http://www.mayoclinic.org/diseases-conditions/cushing-syndrome/basics/definition/con-20032115?reDate=13072015 (3 pages).
Cushing disease definition, MedlinePlus Medical Encyclopedia, retrieved online Jul. 13, 2015, at http://www.nlm.nih.gov/medlineplus/ency/article/000348.htm (5 pages).
Invitation to Pay Additional Fees with Partial Search Report dated Aug. 14, 2015, from International Application No. PCT/US2015/031408 (2 pages).
International Search Report and Written Opinion for PCT/US2015/031408, dated Oct. 30, 2015, 11 pages.
EP15793415.9 , "Extended European Search Report", Jan. 2, 2018, 11 pages.
Boehringer et al., "Automated Syndrome Detection in a Set of Clinical Facial Photographs", American Journal of Medical Genetics Part A, Sep. 1, 2011, 155(9):2161-2169.

*Primary Examiner* — Eric S Dejong
(74) *Attorney, Agent, or Firm* — Kilpatrick Townsend & Stockton LLP

(57) ABSTRACT

Devices, systems, and methods for use in managing treatment of a chronic disorder with pharmaceutical or therapeutic compounds by tracking symptoms associated with the disorder. Methods include inputting patient attributes, factors and various and other data relating to the patient in conjunction with one or more symptoms into a symptom tracking system and outputting a report of the data tracked over time to any of the patient, a medical professional and a drug developer to improve identification of a relapse of the chronic condition and improve management of the treatment regimen for any and all patients.

24 Claims, 23 Drawing Sheets

1/1/2014

2/12/2014

SYSTEMS AND METHODS OF MANAGING TREATMENT OF A CHRONIC CONDITION BY SYMPTOM TRACKING

CROSS-REFERENCES TO RELATED APPLICATIONS

This application is a Non-provisional of and claims priority to U.S. Provisional Patent Application No. 61/994,815 filed May 16, 2014, the entire contents of which are incorporated herein by reference.

BACKGROUND OF THE INVENTION

The present invention generally pertains to management of chronic conditions, in particular chronic conditions that are treated utilizing administration of pharmaceutical or other therapeutic compounds.

While medical treatments utilizing administration of pharmaceutical or therapeutics are widespread, the effectiveness of a given treatment may vary widely from patient to patient, particularly when administered over a long period of time for treatment of a chronic condition. Even when the efficacy of a given treatment has a high degree of predictability in most patients, the success of treatment may still vary considerably based on the patient's compliance with the prescribed treatment as well as the ability of the physician to prescribe an appropriate treatment regimen for a given patient. In addition, certain chronic conditions may vary in intensity over time and patients may experience occasional relapse or an increase in symptoms that require changes in treatment. It can often be difficult to recognize these periods of relapse or increase in symptoms before their effects are full-blown causing escalating symptoms or prolonged periods of relapse unnecessarily. These difficulties can become even more problematic when the effect of a treatment and associated pharmaceutical or therapeutic is less predictable, or vary considerably between patients.

Given the complexities and challenges posed by conventional treatments utilizing administration of pharmaceuticals, there exists a need to improve treatment management of chronic conditions. There further exists a need to provide a means to prevent relapse of the chronic condition.

BRIEF SUMMARY OF THE INVENTION

The present invention generally pertains to management of chronic conditions, particularly those conditions treated by administration of pharmaceutical or other therapeutic compounds. In particular, the invention pertains to tracking of one or more symptoms associated with a chronic condition to facilitate identification of changes in symptoms to improve management of the chronic condition being treated, prevent relapse and improve patient outcomes.

DETAILED DESCRIPTION OF THE INVENTION

Figure 1:
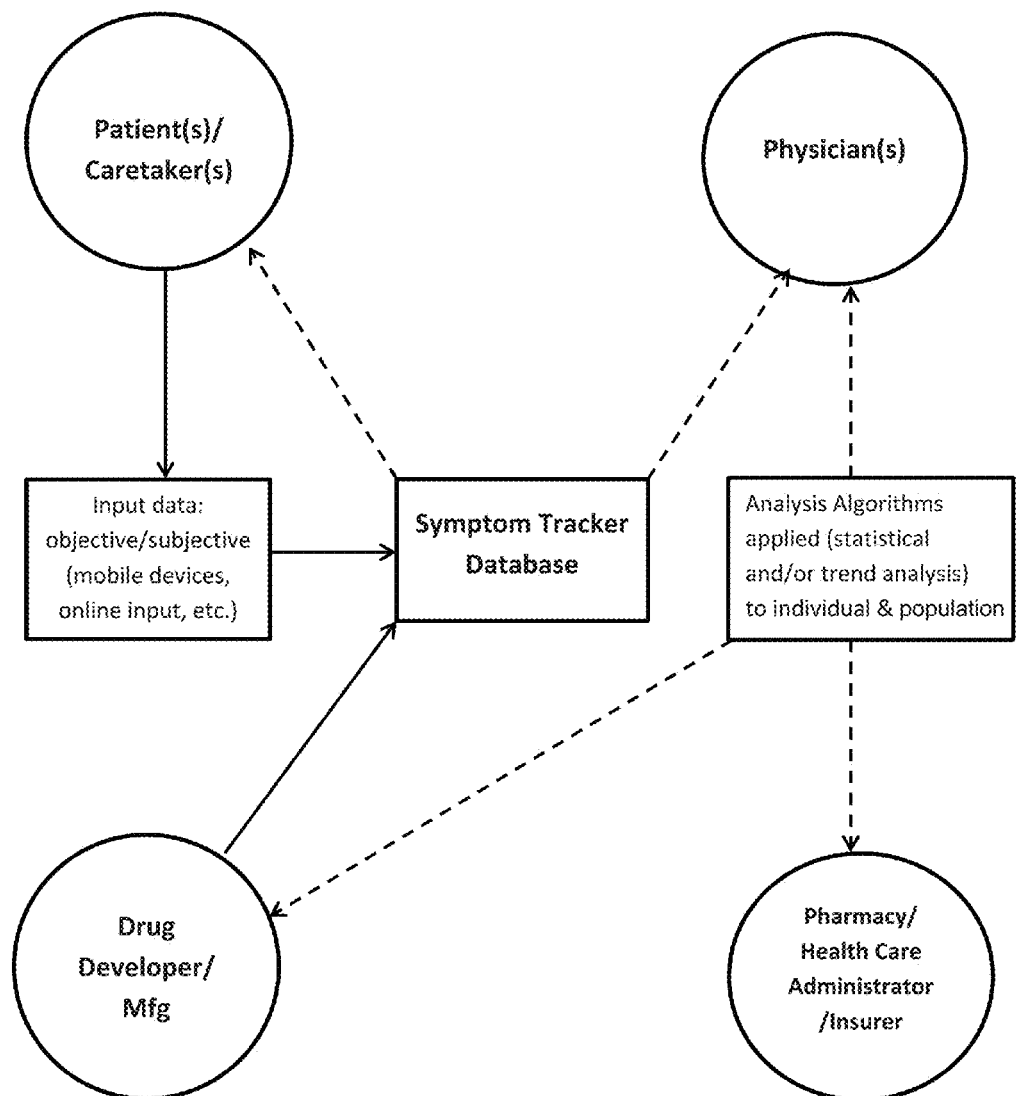
FIG. 1 illustrates a graphical system overview of example embodiment of the invention.

The present invention generally provides a system for use in managing chronic conditions, in particular, conditions treated with one or more drugs or therapeutic compounds. In certain aspects, the system provides a symptom tracking information management system (e.g. database and the like) in which attributes relating to a patient having the chronic condition and symptoms of the patient are received and tracked over time to facilitate monitoring of the condition and an associated treatment regimen. Such information may be output periodically or upon one or more symptoms exceeding a predetermined range or value to alert the patient or medical professional to a change in symptoms or condition in a particular patient that may necessitate further action. Such action may include counseling, follow-up visits, further physiological testing and/or modifications to the treatment regimen. In certain aspects, such information may be collected from multiple patients and analyzed, such as in a statistical analysis, to alert the medical professions or a drug developer to trends, correlations, or interactions between certain patient factors, symptoms and treatment regimens, which may inform and improve prescribed treatment regimens. In another aspect, methods may further include tracking of one or more factors associated with the chronic condition that are monitored independently from or in combination with tracking of associated symptoms. Such factors may include tracking of various compounds within the patient's blood, including but not limited to blood glucose, hormone levels, drug levels and the like. Tracking of one or more additional factors in combination with one or more symptoms may be further advantageous by allowing determination of a correlation between symptoms and the chronic condition and/or the one or more factors or may be used to provide verification of a likely change in the chronic condition indicated by tracked changes in patient symptoms. In some embodiments, any information entered by the patient is accessible to the patient to facilitate tracking of the condition by the patient; all or some of the information is accessible by a medical professional treating the patient; and all or some of the information is accessible to a drug developer. At least some of the information entered by the patient may remain confidential to the patient or to the patient and physician. In some aspects, the information entered by multiple patients is analyzed and output to a drug developer to provide statistical information as to the condition, symptoms and treatment based on one or more attributes of the patient (e.g. age, sex, weight, location, treating physician, treatment duration) or based on one or more attributes of the prescribed treatment regimen.

As referred to herein, the term "symptom" comprises any objective or subjective feature or sign resulting from or of any potential interest in regard to the chronic condition or illness being treated or management thereof. While classically, the term "sign" refers to test results (e.g. blood cell count) or features noticed by those other than the patient, within the context of this disclosure such signs are included within the term "symptom." Such symptoms can be identified by any of the patient, a caretaker, physician, medical professional, or anyone with sufficient exposure to the patient or samples from the patient. In addition, the term "user" refers to any user of the information system, which may include the patient, a caretaker, a medical professional, facility, insurer, pharmacy, drug developer or drug manufacturer or third party.

In one aspect, the system provides a symptom tracking information system in which one or more fields of information relating to a patient, physician and drug treatment are received by the patient and/or medical professional and information regarding one or more symptoms are entered by the patient over time (preferably at regular intervals) and output to the patient and/or physician to facilitate monitoring and assessment of the condition. Such output may be in the form of an e-mailed or printed report and may be provided periodically (e.g. weekly, monthly) or may be output in response to a condition (e.g. change in treatment or physicians, one or more symptoms exceeding a certain value or range, or a certain combination of symptoms). In one aspect, the patient inputs information regarding the one or more symptoms on a regular basis (e.g. weekly) so that a tracking of the symptoms can more accurately reflect stability of the treatment and associated symptoms or an increase in symptoms, which may be indicative of a relapse or a need to modify the treatment regimen (e.g. dosage increase).

An example of a chronic condition that can be difficult to treat is a hormonal disorder, such as Cushing's Syndrome. "Cushing syndrome occurs when your body is exposed to high levels of the hormone cortisol for a long time. The most common cause of Cushing syndrome, sometimes called hypercortisolism, is the use of oral corticosteroid medication. The condition can also occur when your body makes too much cortisol. Too much cortisol can produce some of the hallmark signs of Cushing syndrome—a fatty hump between your shoulders, a rounded face, and pink or purple stretch marks on your skin. Cushing syndrome can also result in high blood pressure, bone loss and, on occasion, diabetes. Treatments for Cushing syndrome can return your body's cortisol production to normal and noticeably improve your symptoms. The earlier treatment begins, the better your chances for recovery." (available online at http://www.mayoclinic.org/diseases-conditions/cushing-syndrome/basics/definition/con-20032115).

A particular form of Cushing's Syndrome is Cushing's disease. "Cushing's disease is caused by a tumor or excess growth (hyperplasia) of the pituitary gland. This gland is located at the base of the brain. People with Cushing's disease have excess ACTH, which stimulates the production and release of cortisol, a stress hormone. Too much ACTH means too much cortisol. Cortisol is normally released during stressful situations. It controls the body's use of carbohydrates, fats, and proteins and also helps reduce the immune systems response to swelling (inflammation). Treatment involves surgery to remove the pituitary tumor, if possible. After surgery, the pituitary may slowly start to work again and return to normal. During the recovery process, a patient may need cortisol replacement treatments. Radiation treatment of the pituitary gland may also be used. If the tumor does not respond to surgery or radiation, the patient may get medications to stop or decrease production of cortisol. If such treatments are not successful, the adrenal glands may be removed to stop excess levels of cortisol from being produced." (http://www.nlm.nih.gov/medlineplus/ency/article/000348.htm).

Treatment of endocrine disorders, such as Cushing's Syndrome, can be particularly difficult to manage due to less predictable patient response to administration of a synthetic steroid, such as mifepristone. Mifepristone is a synthetic steroid that binds progesterone and glucocorticoid receptors and has been employed to treat a number of conditions including meningioma, uterin fibroids, hyperadrenocorticism, metabolic, oncologic, opthamalogic, central nervous system disorders and certain psychiatric illnesses. Examples of such metabolic disorders include diabetes, obesity, antipsychotic induced weight gain, hypertension, and osteoporosis; examples of oncologic illness include various types of cancers, including ovarian cancer and prostate cancer; examples of central nervous system disorders include Alzheimer's Disease, neurodegenerative diseases, post traumatic stress disorder, and alcohol dependence; and examples of opthamalogical conditions include glaucoma and central serous retinopathy. It has been surprisingly discovered that administration of the same dose of mifepristone can produce widely varying plasma drug concentrations in different patients. For a particular dose of mifepristone, the plasma drug concentration can differ by as much as 800% from one patient to the next. The varied plasma drug concentration can result in some patients not receiving an efficacious dose of mifepristone. For these patients in particular, it is necessary to improve the pharmacokinetics of mifepristone upon administration. Treatment with mifepristone can be further understood by reference to the following commonly-owned application: U.S. application Ser. No. 13/677,465 filed Nov. 15, 2012 entitled "Optimizing Mifepristone Absorption," the disclosure of which is incorporated by reference in its entirety. It is understood that the methods and systems of the present invention may be used in variety of treatments, and are particularly advantageous when used with complex and difficult to manage treatments, such as any therapy that requires dose titration over time. The length of such therapies may extend over a period of weeks, months, a year or many years. Another difficult to manage therapy is chemotherapy, which often involves administration of chemotherapy agents in a treatment regimen over three months or more and require tight adherence that may benefit from symptom tracking. Various conditions, illnesses and therapies, including any of those described herein, can be more effectively managed to provide improved patient outcomes by utilizing the symptom tracking methods and systems described herein.

Given the variability of symptoms experienced in a patient having Cushing's syndrome, as well as the varied responses to medication, use of a symptom tracker system, such as described herein, is particularly suited for tracking symptoms associated with Cushing's Syndrome. It is appreciated however that the symptom tracker System may be used with various other chronic conditions, particularly conditions that can exhibit seemingly unpredictable variability in symptoms and/or responses to medications, including but not limited to various types of inflammation, such as arthritis; disorders of the skin, such as psoriasis; blood, kidney, eye, thyroid, and intestinal disorders (e.g., colitis); allergies; multiple sclerosis; and asthma.

In one aspect, the Symptom Tracking System utilizes an image-based tracking feature that is particularly useful for diagnosis and management of chronic diseases or conditions that exhibit noticeable changes in appearance. In particular Cushing's Syndrome, a pituitary gland disorder often causes increases in facial fat resulting in a rounded facial appearance often referred to as "moon face." In Cushing's Syndrome, prolonged exposure to high levels of the hormone cortisol result in rapid weight gain, particularly in the trunk and face. A common symptom of Cushing's is the growth of fat pads along the collarbone, the back of the neck and the sides of the face resulting in a widened, rounder face. While a hallmark sign of Cushing's, these changes can be difficult to recognize over long periods of time or differentiate from normal weight gain, particularly if a patient's in-person visits to a clinician are infrequent. Since Cushing's may be caused by various factors (pituitary disorder, response to medications, tumor, or trauma to the pituitary gland), treatments for Cushing's vary and may include surgery and/or medications. In patients where surgery is not suitable, patients typically are treated by medications and their progress is monitored. Maintaining proper levels of cortisol can be challenging, however, and hormone levels and symptoms must be monitored closely to track progress and manage treatment as needed.

In one aspect, any outwardly visible symptoms may be tracked by image-based tracking and optionally analyzed by the system. Typically, the patient obtains images and uploads the images to the symptom tracking system. Obtaining a self-image with a smartphone and uploading by smartphone is a relatively quick and simple way of recording objective data of the patient's facial appearance to help the patient and/or the medical professional track their progress and assess general trends in the patient's condition based on facial appearance. Such images may allow identification of relatively minor physical changes that other physiological measurements may not readily identify. In addition, these changes can be identified by the system without requiring frequent in-person visits to the clinician. Since in Cushing's Syndrome, the patient may experience an increase in size and thickness in fat pads on the sides of their face or on the back of their neck which is disproportionate from regular weight gain, this development can be more readily identified in a progression of photographs than merely from merely tracking weight gain in general, particularly since a patient's weight may fluctuate for a variety of reasons unrelated to the chronic condition (e.g. depression, life changes, injury, etc.) While this image-based feature relates to outwardly visible symptoms observable from an image, it is appreciated that various other symptoms suitable for tracking in accordance with the methods described herein are not necessarily outwardly visible and may be determined from various other means, including but not limited to various types of testing (e.g. blood testing, blood pressure, physical testing/examination, etc.).

This image-based tracking feature assists in diagnosis and tracking of the outward symptoms of Cushing's by comparing images of the subject over time and monitoring the type and magnitude of changes in physical appearance, especially changes in facial appearance. These changes may be difficult to quantity and to distinguish from ordinary changes in weight. The tracking system should be capable of recognizing the patient's face sufficiently to allow comparison between images to identify relatively small changes in facial appearance between images. For example, the system may run a "facial recognition subroutine" that may recognize the imaged face and/or normalize the images to allow direct comparison between images. The images may be obtained by a user at home with an integrated laptop camera or web camera and uploaded onto a server and associated with a user account to allow tracking of the user's symptoms. By comparing a series of images over time, the tracking system can monitor and track subtle changes and general trends that would be difficult to quantify otherwise and assist in monitoring and treatment of the condition. In addition, tracking the symptoms over time allows the patient or medical professional to monitor the progress of the syndrome as well its response to treatment so that treatments can be adjusted as needed to improve patient outcomes.

In one aspect, methods include image-based tracking of symptoms relating to outward physical appearance using a series of images uploaded by the patient over time into the symptom tracking system. In certain aspects, methods of determining changes in facial shape that may be attributable to Cushing's Syndrome include any or all of the following: tracking of changes in facial shape/appearance based on series of images over time; methods for determining increased fat deposits based on comparison between images; methods for normalizing a series of images to allow comparison of features between images; methods for tracking progression of symptoms based on changes in outwardly visible symptoms; methods for prescribing treatment based on history of tracked visual symptoms and past treatment; methods/systems utilizing a "facial recognition routine" to allow comparison between facial images; and a web-based system allowing user to upload images, compare changes between images to determine symptoms and provide tracking history of symptoms to user and/or medical professional.

Management of a chronic condition using a Symptom Tracking System in accordance with aspects of the invention can be further understood by reference to FIG. 1, which illustrates a flow chart of an example symptom tracking system. This system includes a symptom tracking information system provided by the developer of a pharmaceutical used in treatment of the chronic condition in which fields of information are input by a user (typically the patient, although a patient and physician may work together to establish a profile). In this example, the system is accessible online by a patient such that the patient establishes a patient profile in the symptom tracking system maintained by the drug developer and symptom information on the selected symptoms is routinely input by the patient over time. The information is stored by the system and reports based on the data are output to any of the patient, physician or developer upon request, the differing in type and information based on the recipient and/or query. In certain aspects, the system analyzes the symptom information according to one or more algorithms or relationships stored in a processing unit of the system. The relationships or algorithms may be determined by the processing unit based on statistical analysis of the information or may be input by or more entities as they become known, such as through clinical studies. In this example, the information and algorithms are input on a symptom tracking information system maintained by the drug developer, although it is appreciated that the information and algorithms input into the system can be received from various different entities or uploaded automatically from various other information sources.

In one aspect, the management methods and symptom tracking system described herein may incorporate any aspect of the information systems described in U.S. Provisional 60/880,785 filed Sep. 20, 2013, entitled "Systems and Methods of Treatment Using Intervention Determination and Tasking," the entire contents of which are incorporated herein in its entirety.

In another aspect, the system allows for analysis of one or more symptoms over time to determine a trend or certain combination of symptoms for use by the physician in treating the particular patient or to determine statistical information that may be used by the physician or the drug developer to improve treatment regimens. In one aspect, data relating to one or more symptoms entered by a patient may be directly accessible by the treating physician on an as needed basis or may be obtained by the physician from reports produced on a periodic basis or in response to a trigger condition, such as a symptom exceeding a specified range or value relative to a baseline. In another aspect, the system may provide the physician with analyzed data, such as a trend of one or more symptoms over time, to assist the physician in making a determination of the patient's condition and/or the efficacy of treatment. In yet another aspect, the system may perform a statistical analysis on the data entered by multiple patients and provide sortable data or provide results from a statistical analysis of the one or more patient symptoms or treatment efficacy in relation to a patient attribute.

FIG. 1 illustrates a flow chart in an example symptom tracking system. The symptom tracking system may include a symptom tracking information system provided and supported by the drug developer or manufacturer and made accessible to the patient(s), physician(s), medical facility or third parties online, such as through a mobile device app or an online portal. The user may input data into the system, for example a patient or caretaker may input symptoms through a computer accessing the online system or through the mobile device or smartphone application. The information is stored in the symptom tracker information system, along with information input by numerous other patients. The information may be associated with various identifiers or attributes (e.g. patient name, physician, condition, treatment, geographical location, etc.) so as to allow further analysis, such as statistical analysis or trend analysis, based on a community or subset of patients. In another aspect, determining community trending or statistics based on geographical location is particularly useful in administrative management of treatment administration by the drug developer, manufacturer, pharmacy, health care administrator and insurer. In some aspects, the physician may input data into the system (not shown). The information may then be output to a user of the information system, shown in dotted line, in the form of reports or various other means, which may take the form of visual displays on computer screens, touchpads, mobile devices, e-mails, written print outs or other means of communicating information to the user. The information may be output directly to the user, such as user input data in summary or timeline form, or the information may be analyzed, such as by an algorithm, statistical or trend analysis, before being output to the user in a report. The output data may include information pertaining to a particular patient or to a patient community, such as information pertaining to a community of patient of which the particular patient is included, or as to any community of patients of which the user requests information. The report may be output periodically or may be output in response to a particular condition of a patient or community, or in response to a query by a user. It should be noted that the information may be output to any user, in many different types or formats by various different means depending on the data and the user.

In one aspect, the system is configured to allow one type of user to contact another type of user. For example, after viewing reported info, the physician may utilize the system to contact the patient, or may input data associated with the patient profile (such as an update in regard to the treatment regimen or a message to the patient). In another aspect, the drug developer or manufacturer may contact the patient directly through the system, such as to provide information regarding the treatment regimen or management of treatment, to schedule a physician follow-up or to provide patient support. This may be performed in response to a report from the system that the patient is in a vulnerable patient population, such as may be based on a noted trend in symptoms or a community trend. Contact with the patient may be performed through the patient profile, such as by a message that appears when the patient logs onto their profile in the system to enter data. The system may be configured to allow one type of user to contact another type or different types of users, such as the drug developer contacting each or any of the patient, the physician and the pharmacy. Such contact may include a report output to the specified user or may further include additional information or instructions.

According to some embodiments, the symptom tracking information system is provided as an online accessible system maintained on a server and/or on a cloud-based systems. A cloud server may be useful for providing information and advanced information process to a variety of different users accessing the device from various different systems. Different types of data may be accessible to different types of user and/or based on where the user is accessing the system. In another aspect, privileges may be used to protect patient data and/or community data. Dependent upon the privileges associated with their roles (e.g., doctors, insurance agents, patients, or third party data analysts or researchers), different participants may be limited to access only a portion of information relating to the images or a subset of the processing tools without compromising the privacy of the patients associated with the patient information.

According to some embodiments, a server and/or cloud-based system includes a data gateway manager to automatically and/or manually transfer information to/from data providers. Such data gateway management may be performed based on a set of rules or policies, which may be configured by an administrator or authorized personnel. In one embodiment, in response to updates to patient information or treatment regimens, the data gateway manager is configured to transmit over a network (e.g., Internet or intranet) the updated information, such as an updated symptom tracking report. In addition, the data gateway manager may further transfer data amongst multiple data providers that are associated with the same entity (e.g., multiple parties associated with one type of user, such as physicians or the drug developer). The gateway manager may comprise a router, a computer, software or any combination of these components.

Figure 2A:
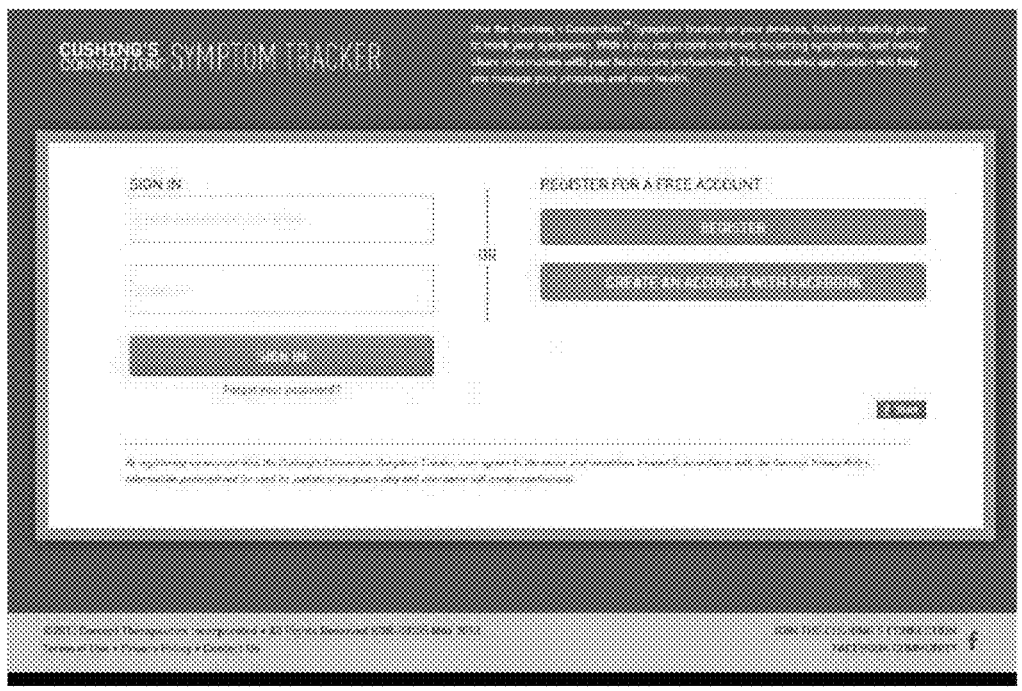
FIGS. 2A-2C illustrate screenshots of an example symptom tracking system for management of a chronic condition relating to establishing a patient profile.
Figure 2B:
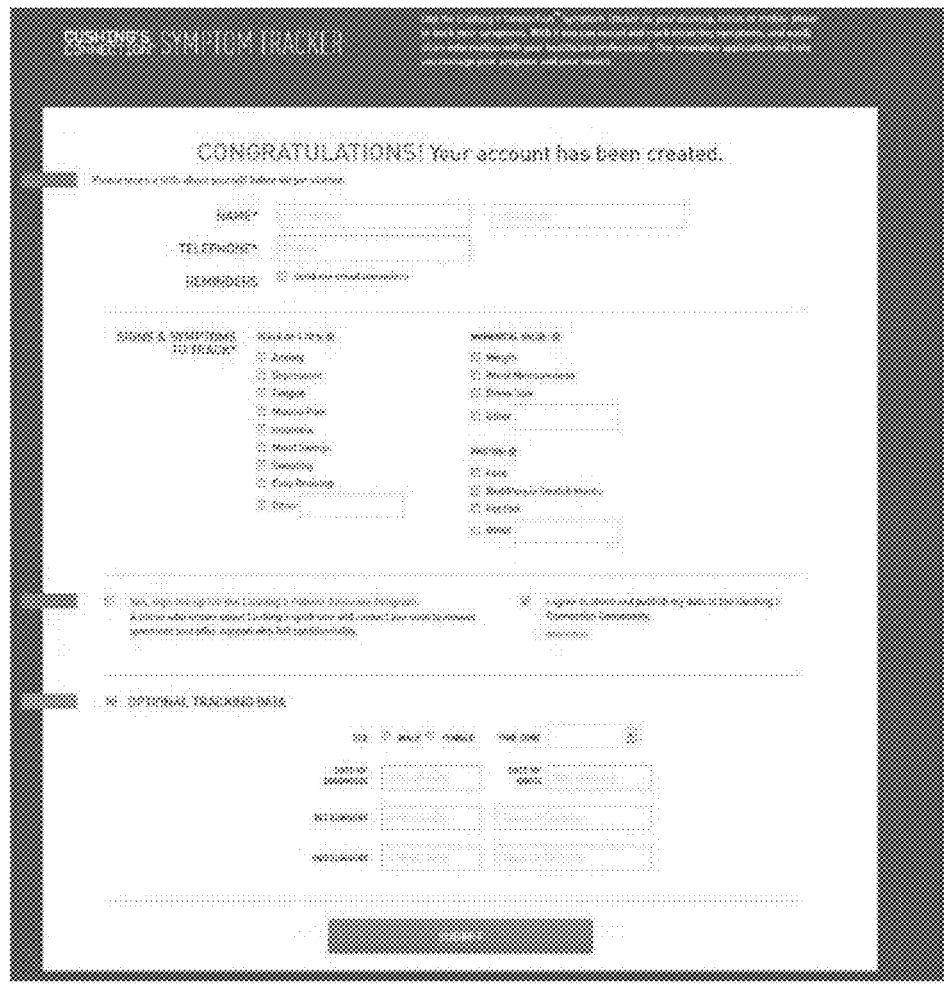
Figure 2C:
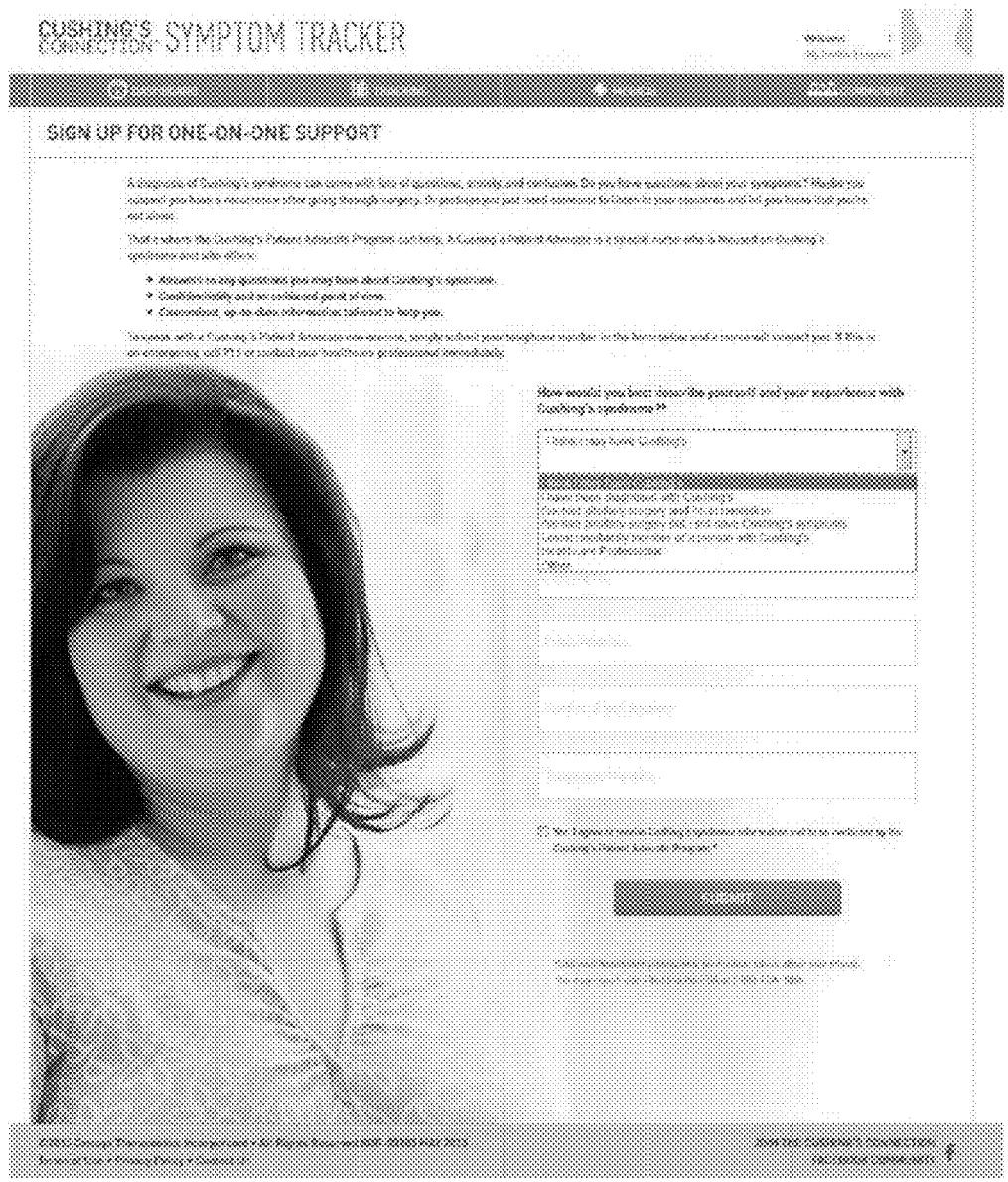

FIGS. 2A-2C illustrate screenshots as would be seen by the patient when accessing the symptom tracker system online to establish a patient profile. As can be seen in FIG. 2A, the account may be linked to an e-mail of the patient, to a Facebook account or Facebook support group (e.g. Cushing's Connection). Upon registering, the patient may select what types of symptoms should be tracked, such as shown in FIG. 2B. A physician may assist the patient in determining which symptoms to track or in selecting the symptoms on the patient's profile. The patient may also track various other types of information such as date of diagnosis, dates of surgery and treatment regimen. The more details the patients adds to the profile, the more effectively the patient and/or medical professional can track the patient's symptoms, condition and progress during treatment. When tracking the signed and symptoms, the patient rates each of the signs and symptoms on a scale of 1 to 5.

In one aspect, the signs and symptoms tracking may include tracking of physiological measurements, including but not limited to weight, blood pressure, and waist size. These are physiological measurements that may be obtained by a device used in the patient's home or at a medical facility and automatically uploaded to the patient's profile, or more typically, may be measured by the patient at home and input into the system by the user. In one aspect, the patient is directed to record certain physiological measurements at regular intervals, for example weekly or daily weight measurements obtained at about the same time of day. This improves accuracy of physiological measurements and allows the patient and/or medical professional to more accurately determine trends over periods of time as opposed to normal daily, monthly or seasonal fluctuations. In another aspect, the patient may record subjective attributes of their condition, for example, the patient may record how they are feeling physically (e.g. energetic, tired, or a "normal" baseline) and/or how they are feeling emotionally (e.g. happy, sad, depressed, etc.), which may also correlate with changes in weight or various other physiological measurements.

In another aspect, the system may further provide registration to and/or access to one-on-one support or patient outreach programs, such as shown in FIG. 2C, to further improve patient compliance with the Symptom Tracking System and improve patient outcomes.

Figure 3A:
FIGS. 3A-3C illustrate screenshots of an example symptom tracking system for management of a chronic condition relating to the patient dashboard, profile and facial image information.
Figure 3B:
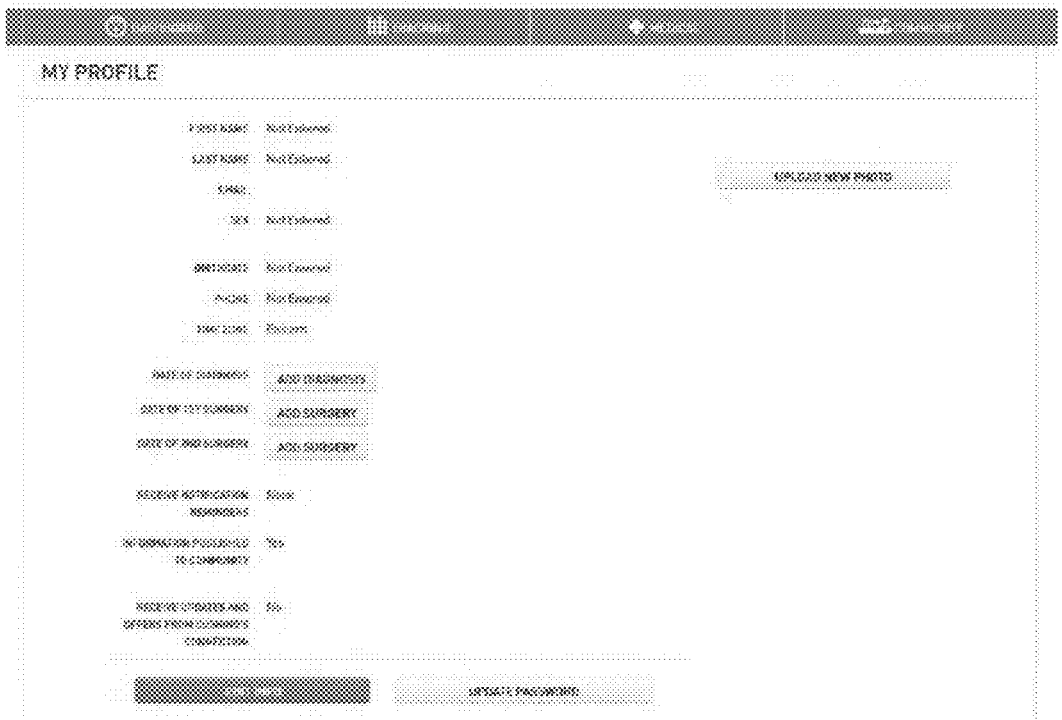
Figure 3C:
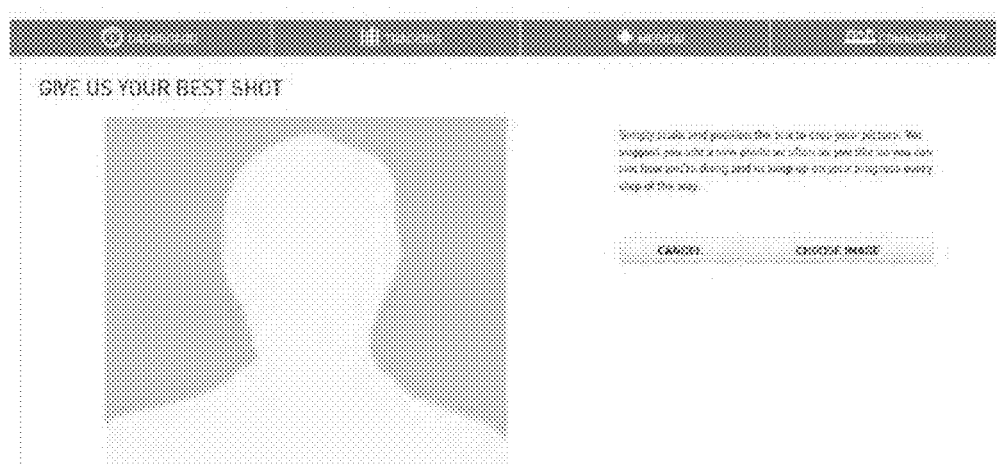
Figure 4:
FIG. 4 illustrates screenshots of an example symptom tracking system for management of a chronic condition relating to selection and entry of symptoms by the patient.
Figure 5A:
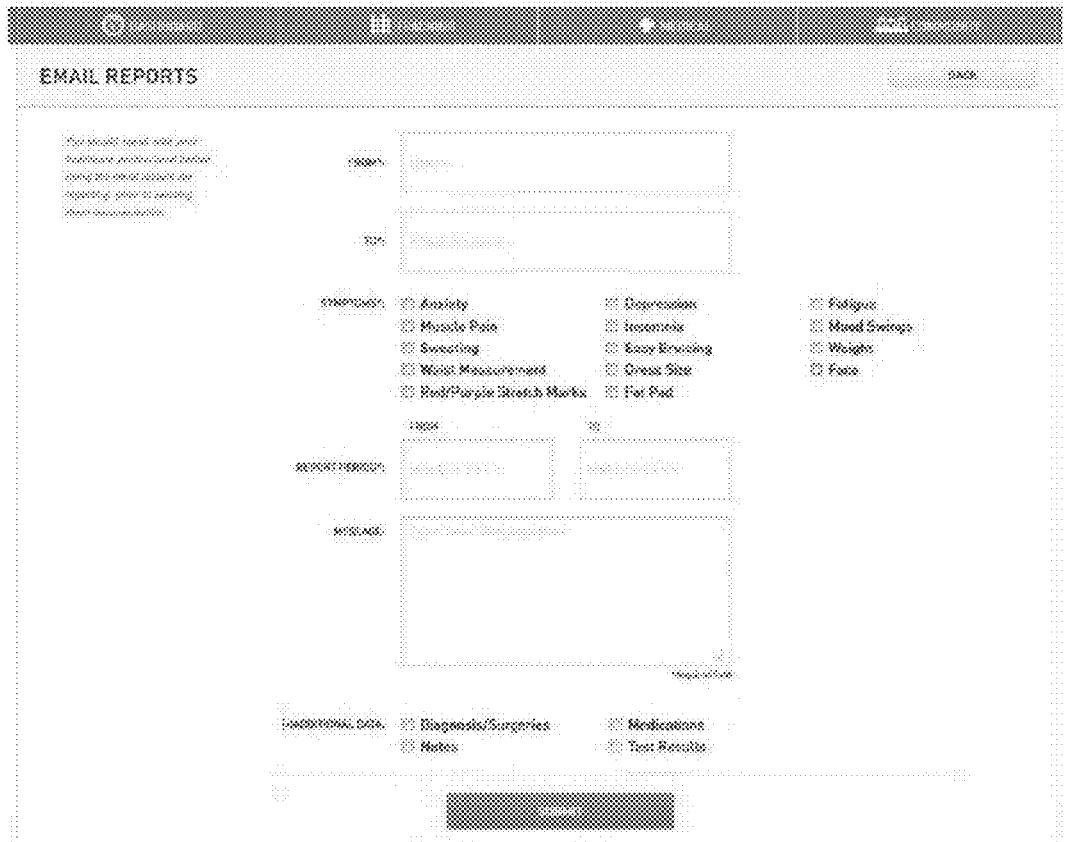
FIGS. 5A-5B illustrate screenshots of an example symptom tracking system for management of a chronic condition relating to reports or alerts regarding tracked symptoms.
Figure 5B:
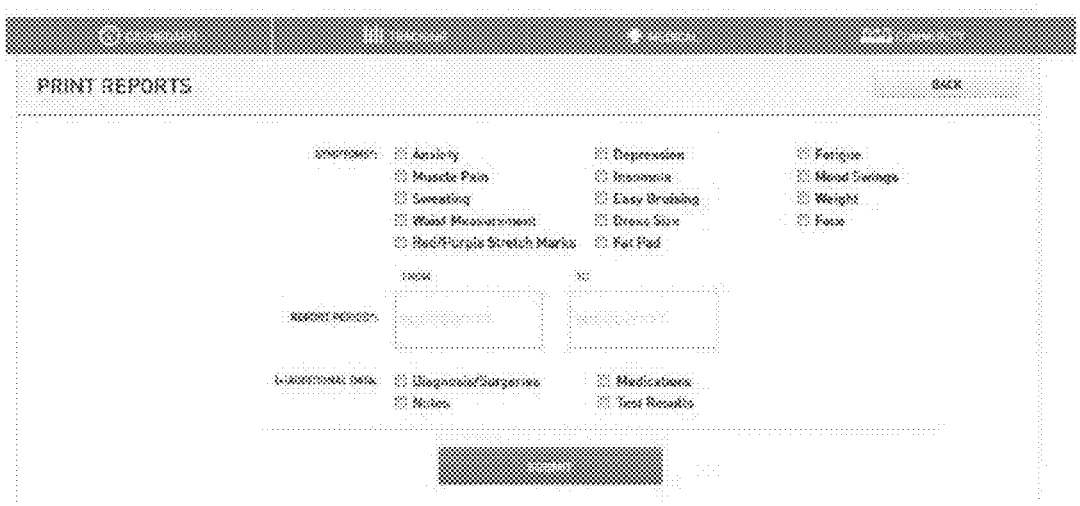
Figure 6A:
FIGS. 6A-6C illustrate a screenshot of an example symptom tracking system for management of a chronic condition relating to tracking of patient symptoms over time and establishing a baseline and goal to assess progress.
Figure 6B:
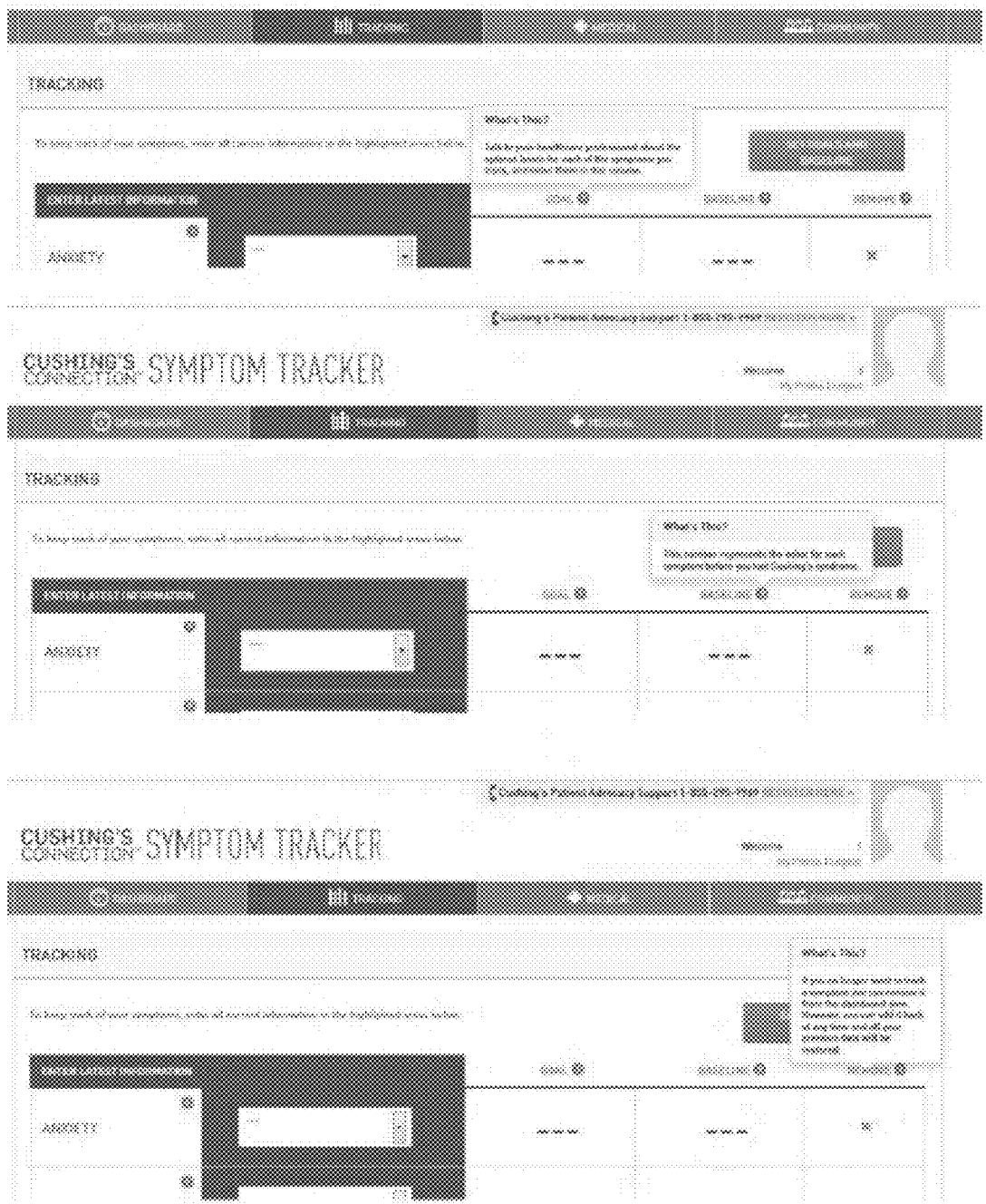
Figure 6C:
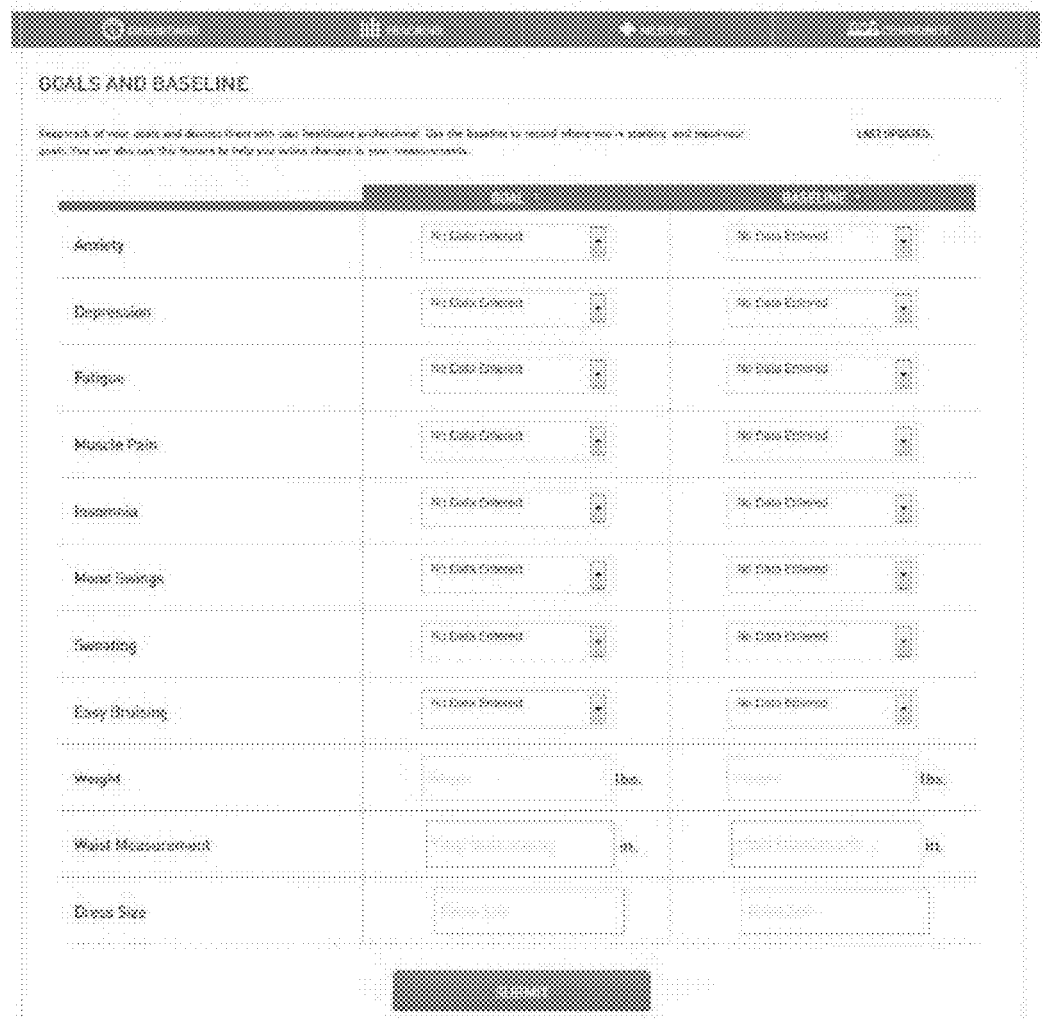
Figure 7A:
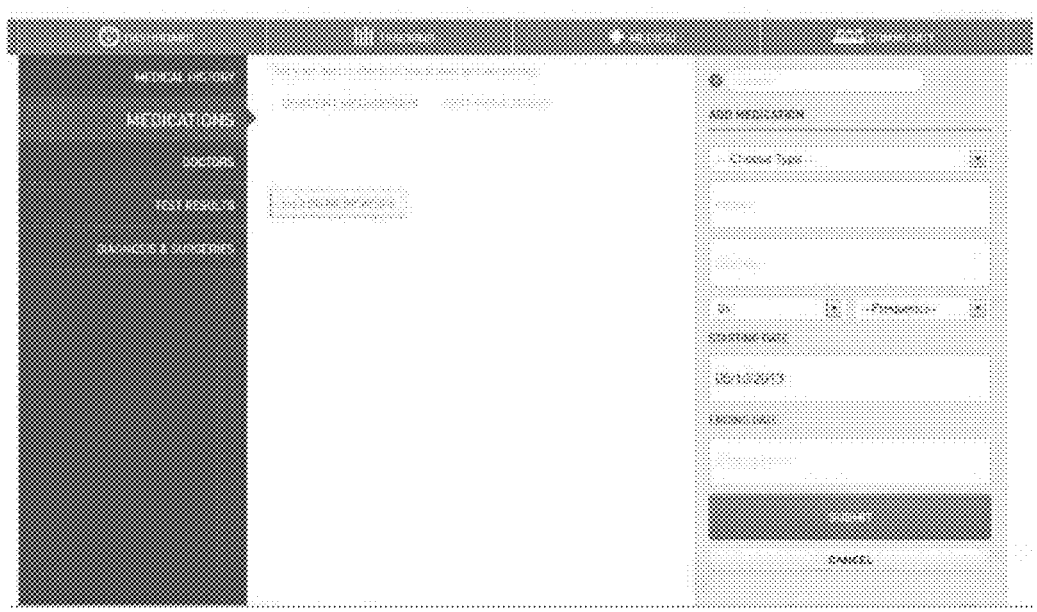
FIGS. 7A-7D illustrate screenshots of an example symptom tracking system for management of a chronic condition relating to entry of patient data to further inform symptom tracking and assessment.
Figure 7B:
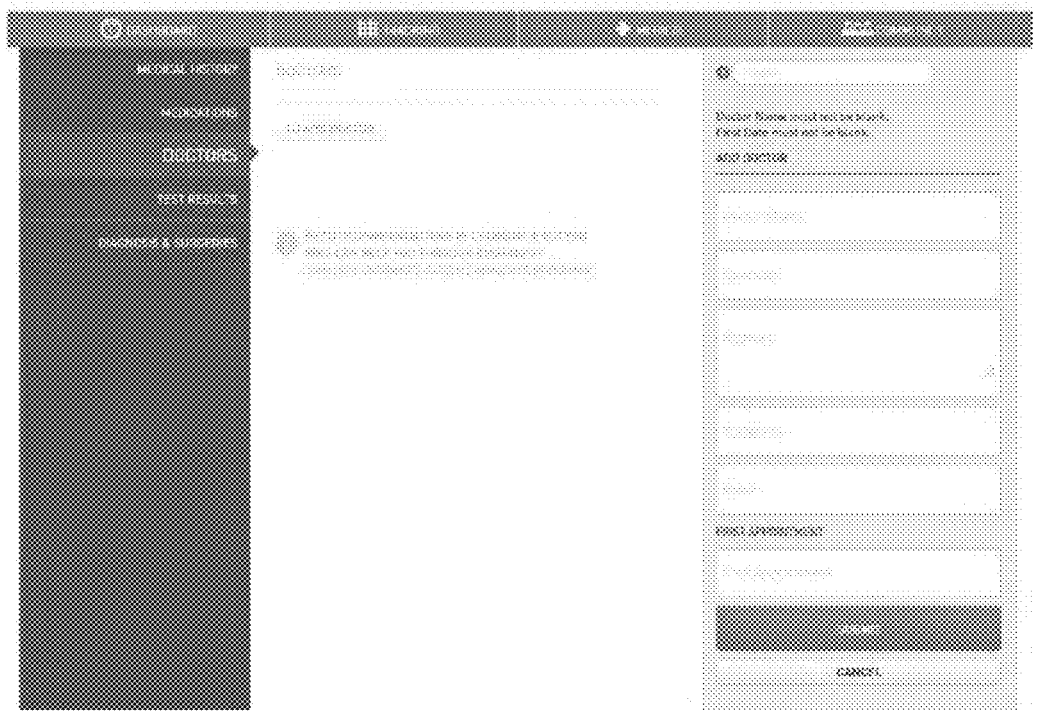
Figure 7C:
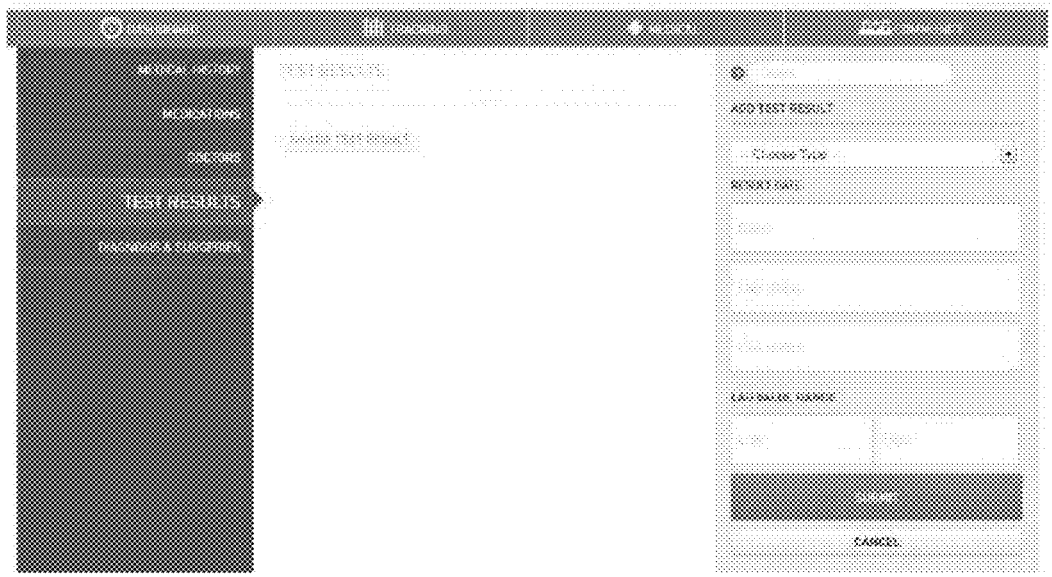
Figure 7D:
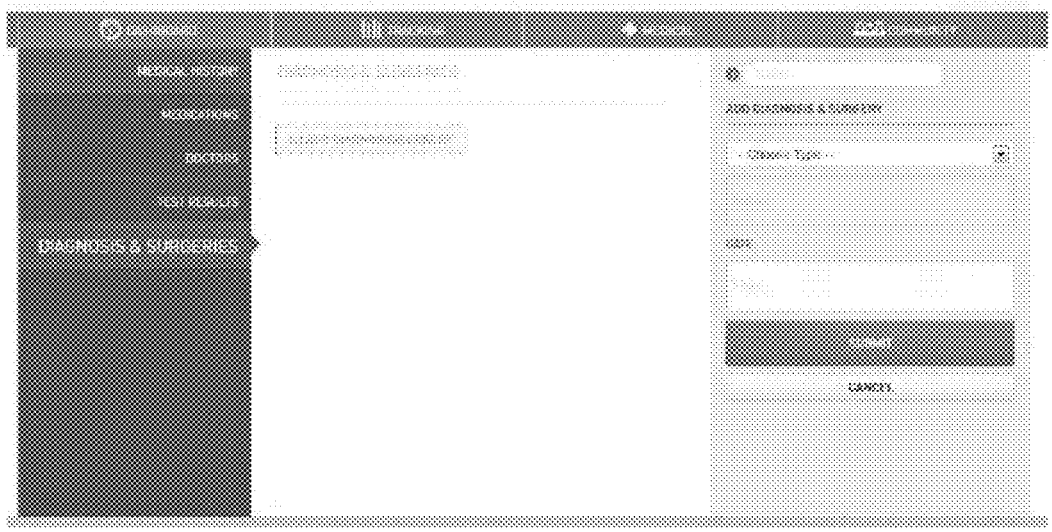
Figure 8:
FIG. 8 illustrates a screenshot of a statistical analysis report output by an example symptom tracking system for use in management of various aspects of treatments for chronic conditions.
Figure 9A:
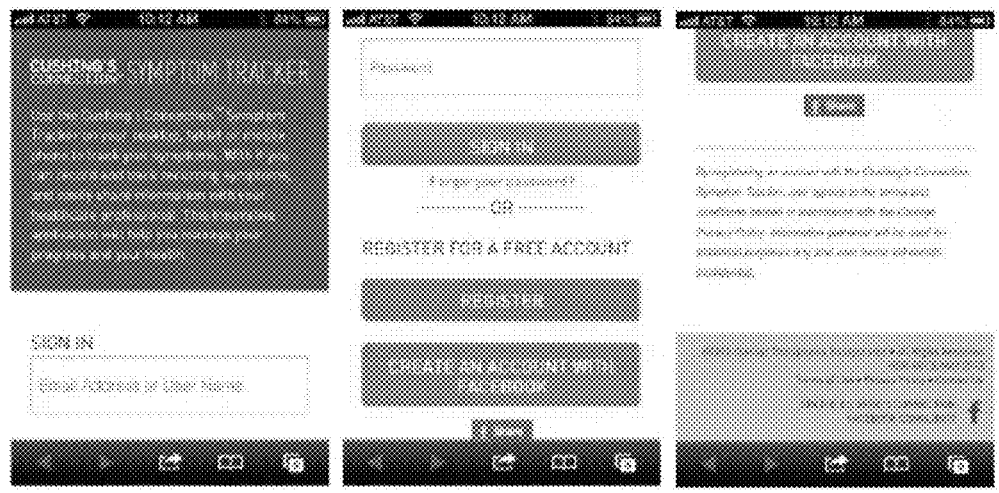
FIGS. 9A-9K illustrate screenshots of an example symptom tracking system as displayed on a patient's smartphone to allow entry and monitoring of data in the system.
Figure 9B:
Figure 9C:
Figure 9D:
Figure 9E:
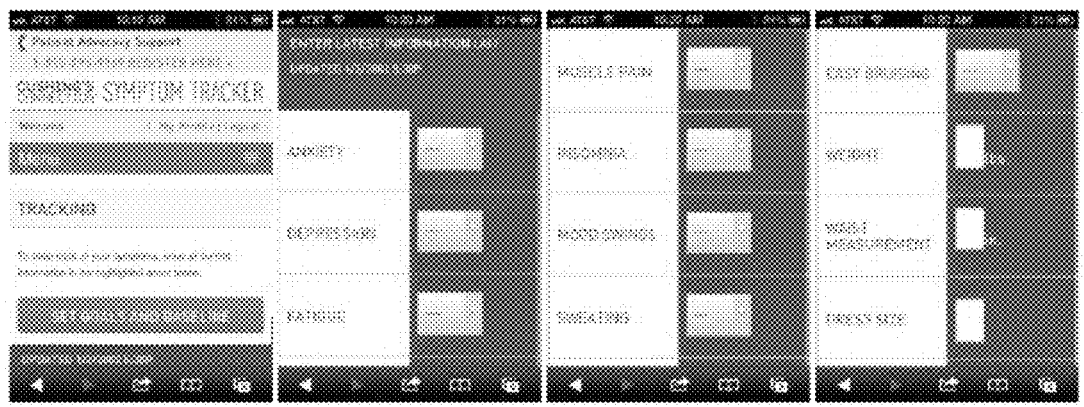
Figure 9F:
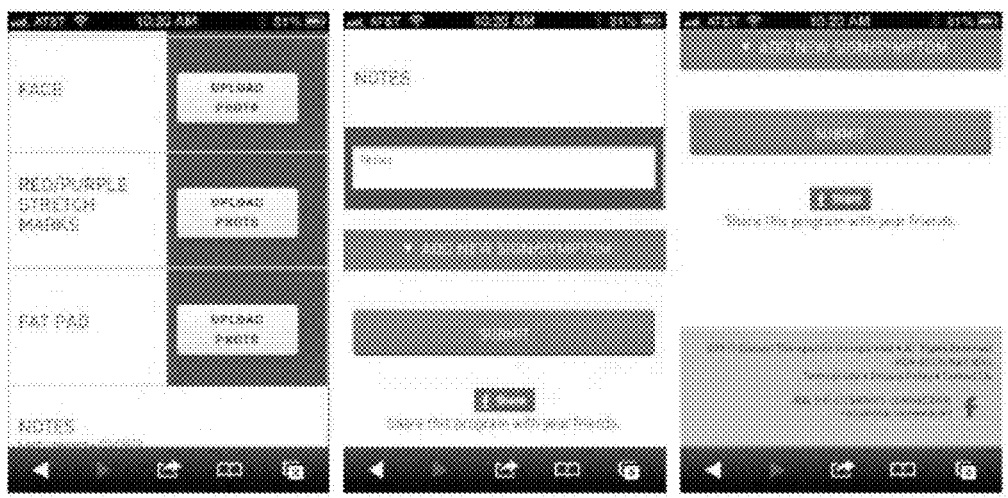
Figure 9G:
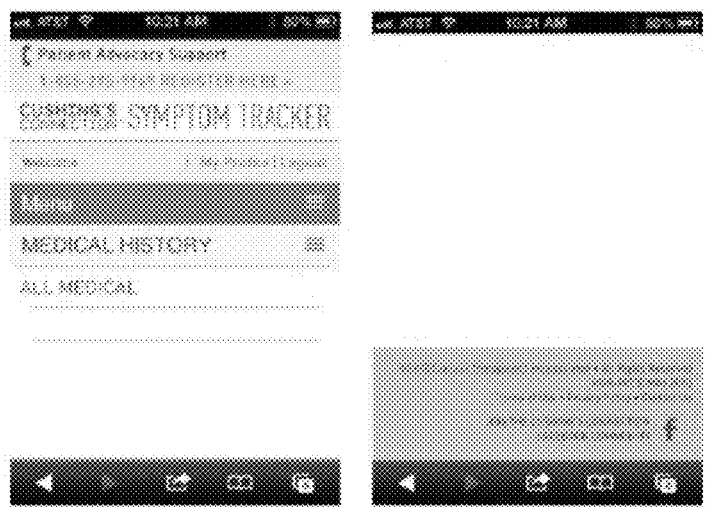
Figure 9H:
Figure 9I:
Figure 9J:
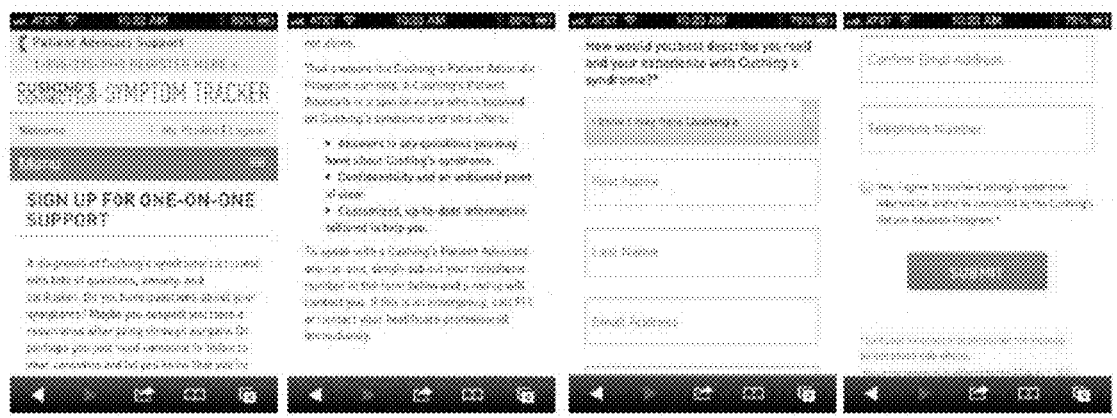
Figure 9K:

In some aspects, the patient may enter various additional attributes that may be useful for monitoring and analysis of the data by the physician and/or in a statistical analysis for use by the drug developer, such as shown in FIG. 3B. In some embodiments, the patient may also set whether to receive notification and reminders as to information regarding treatment and/or their personalized symptom tracking Since patient's having Cushing's often have gradual changes in facial appearance, such as an increase in fat pad thickness, the patients are encouraged to select facial appearance as a symptom and to record images of the their face over time, such as shown in FIG. 3C. The images can be readily obtained with a smart phone of the patient and uploaded using a smartphone app linked to the symptom tracking system (see screenshots of such a mobile app in FIGS. 9A-9K).

Figure 10:
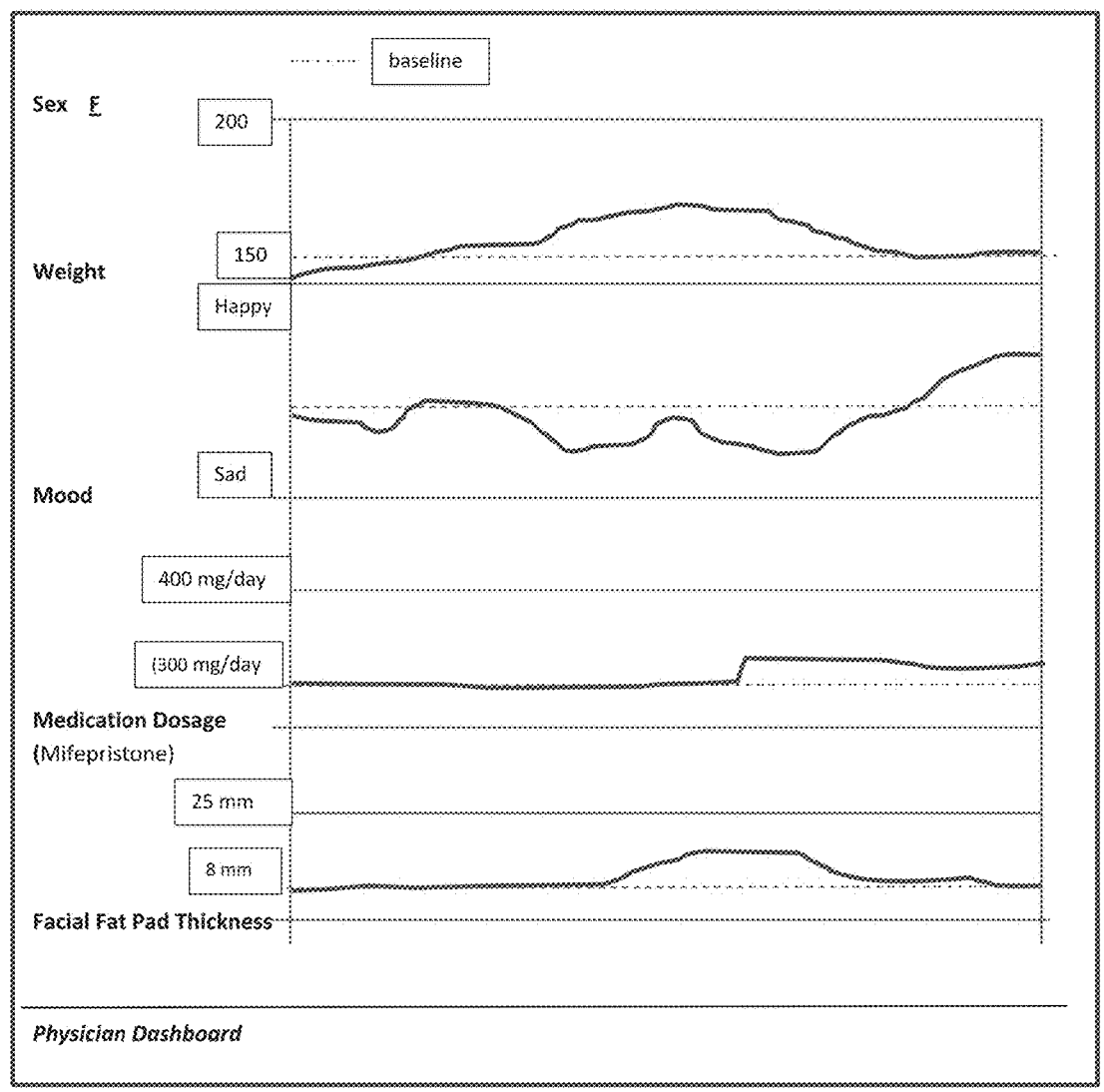
FIG. 10 illustrates an example report output by the example symptom tracking system on a physician dashboard displaying multiple symptoms over time to facilitate monitoring and assessment of the condition and associated treatment.

In one aspect, the images can be later viewed by the patient, physician or drug developer in a format that allows changes in facial dimensions, size and shape to be readily observed by the viewer. For example, the images may be displayed simultaneously in chronological order, such as in the photo timeline display shown in FIG. 11. Such a display format allows the patient and/or physician to more readily recognize changes in facial shape that may be disproportional from normal weight gain. In addition, since weight may fluctuate for a variety of reasons, it may be further useful to track other attributes or possible factors that relate to the one or more selected symptoms but that may also be independent of the chronic condition. For example, by tracking a patient's mood (e.g. anxiety level, depression), it may be determined that a change in weight may correlate more closely an emotional state rather than a poorly regulated hormonal level. Since interactions may be complicated, the reports provided to a patient or the physician may include multiple symptoms and patient attributes displayed simultaneously to assist in determining the possible causes and correlations of the symptoms, such as shown in FIG. 10. These changes are typically assessed by establishing a baseline for each symptom and/or attribute by which to compare the variations in the symptom and/or patient attribute. In some aspects, the patient or physician may establish a goal for a symptom/attribute. While the actual causes of certain symptoms must often be assessed further in patient counseling and/or through further testing (e.g. endocrine or hormonal testing), such reports are particularly advantageous in alerting both the patient and physician to possible interactions between factors or to correlations that would otherwise escape notice. In addition, the continuous monitoring of these symptoms by both the patient and physician using the Symptom Tracking System allows subtle changes to be identified more quickly than would they would otherwise, thereby allowing the physician and patient an opportunity to adjust a regimen or improve patient compliance and prevent relapse of the condition or to reduce the length of a relapse before symptoms escalate.

In another aspect, the factors tracked may be certain compounds in the patient's blood over time for use in diagnosis and/or treatment. Such factors may include: blood glucose measurements, in particular hBa1z and OGTT; hormones that provide an overview of the activity of the HP-axis, which may include but are not limited to, ACTH, CRH and DHEA-S; and various proteins, RNA molecules, or other compounds, such as FKBP51, mRNA and GILZ mRNA, which allow the physician to better understand the downstream effects of cortisol activity in the body. It is appreciated that tracking of these factors may be analyzed in isolation, or in combination with various other patient attributes and/or symptoms described herein. For example, tracking of one or more of the above noted compounds in the patient's blood can provide a more comprehensive picture of the patient's state when combined with tracking of the patient's subjective data (e.g. moods, pain), or when combined with image-based monitoring (e.g. changes in the shape or size of the patient's face). By analyzing these seemingly disparate factors, attributes and/or symptoms over a long period of time, trends and associations that may not otherwise be appreciated from periodic patient interviews can be determined. Such associations and trends are particularly useful in difficult to manage treatments, such as those described herein.

In another aspect, the symptom tracking system may employ algorithms to more accurately determine subtle changes in facial dimensions of the patient over time from the multiple images uploaded by the patient. Since certain facial dimensions remain constant (e.g. distance between eyes, distance between eyes and nose), image analysis algorithms can be used to determine facial dimensions of changeable portions of the face (typically the sides of the face) to determine an increase in width of the face over time. This feature allows for early identification of an increase in the fat pads on the sides of the face. Existing facial recognition algorithms can be used to identify the locations of eyes and to measure a distance between the eyes and the sides of the face, as well as the overall height of the face in each of the images. The measurements can be compared between images to determine an overall trend in change of the size, and in particular the width of the face. This trend can also be represented be displayed as a value or as a graph within another type of report, such as that in FIG. 10 so that the physician or patient can be alerted to changes in facial shape without actually viewing the facial images.

Figure 11:
FIG. 11 illustrates an example report output by the example symptom tracking system on a physician dashboard displaying facial images over time to facilitate monitoring and assessment of facial appearance symptoms associated with the condition.
Figure 12:
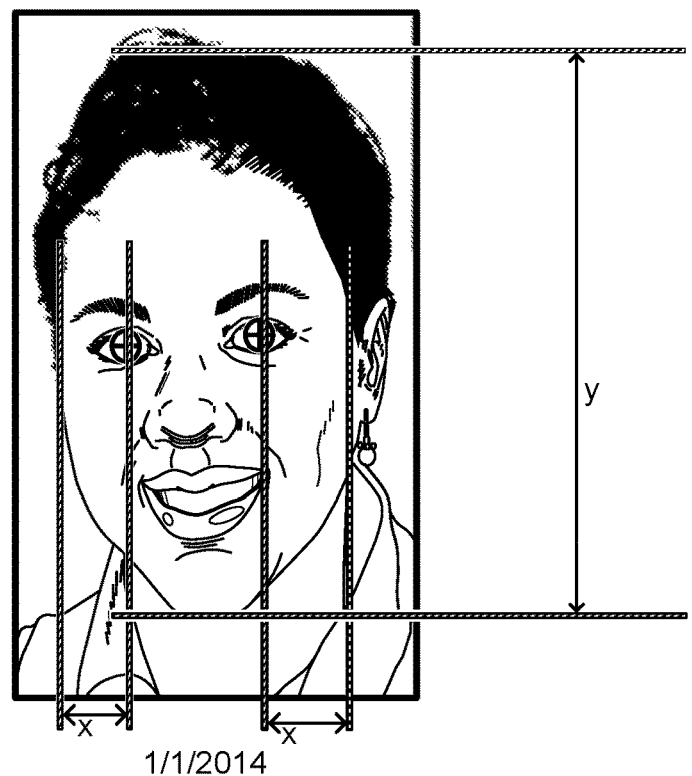
FIG. 12 illustrates an example of an automated analysis of the facial systems to determine changes in facial dimensions or shape over time to facilitate monitoring and assessment of facial appearance symptoms associated with the condition.
Figure 12:
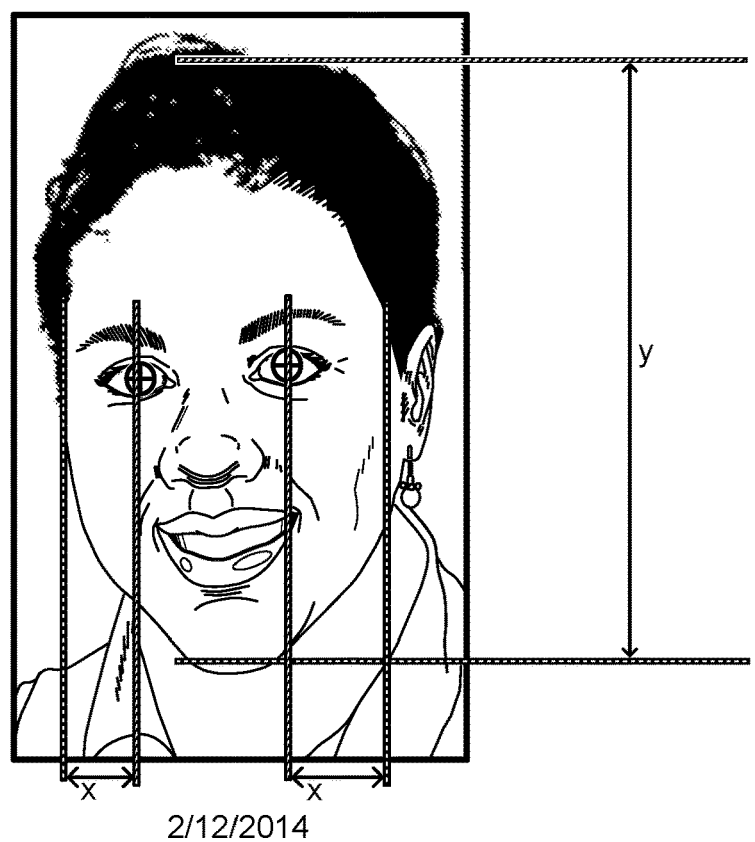

In another aspect, various symptoms, attributes and factors, such as those displayed in the reports in FIGS. 10 and 11, can be assigned a numerical value within an algorithm such that the system could produce an alert to an impending relapse without requiring the patient or physician to actually view the symptom or attribute data in advance. In some aspects, the system may alert the patient or physician to review one or more types of reports in response to a determination that any of the symptoms or patient attributes input by the patient exceed a certain threshold value or range of values (e.g. +/−10% of the baseline value). Advantageously, the system may allow the user, whether the patient, physician or drug developer, to customize a report by selecting which symptoms, attributes or combinations thereof, are desired to be tracked, viewed or analyzed. In some embodiments, the system may analyze the patient attributes and symptoms and determine which are statistically relevant and outputs such attributes/symptoms to the user.

Figure 13:
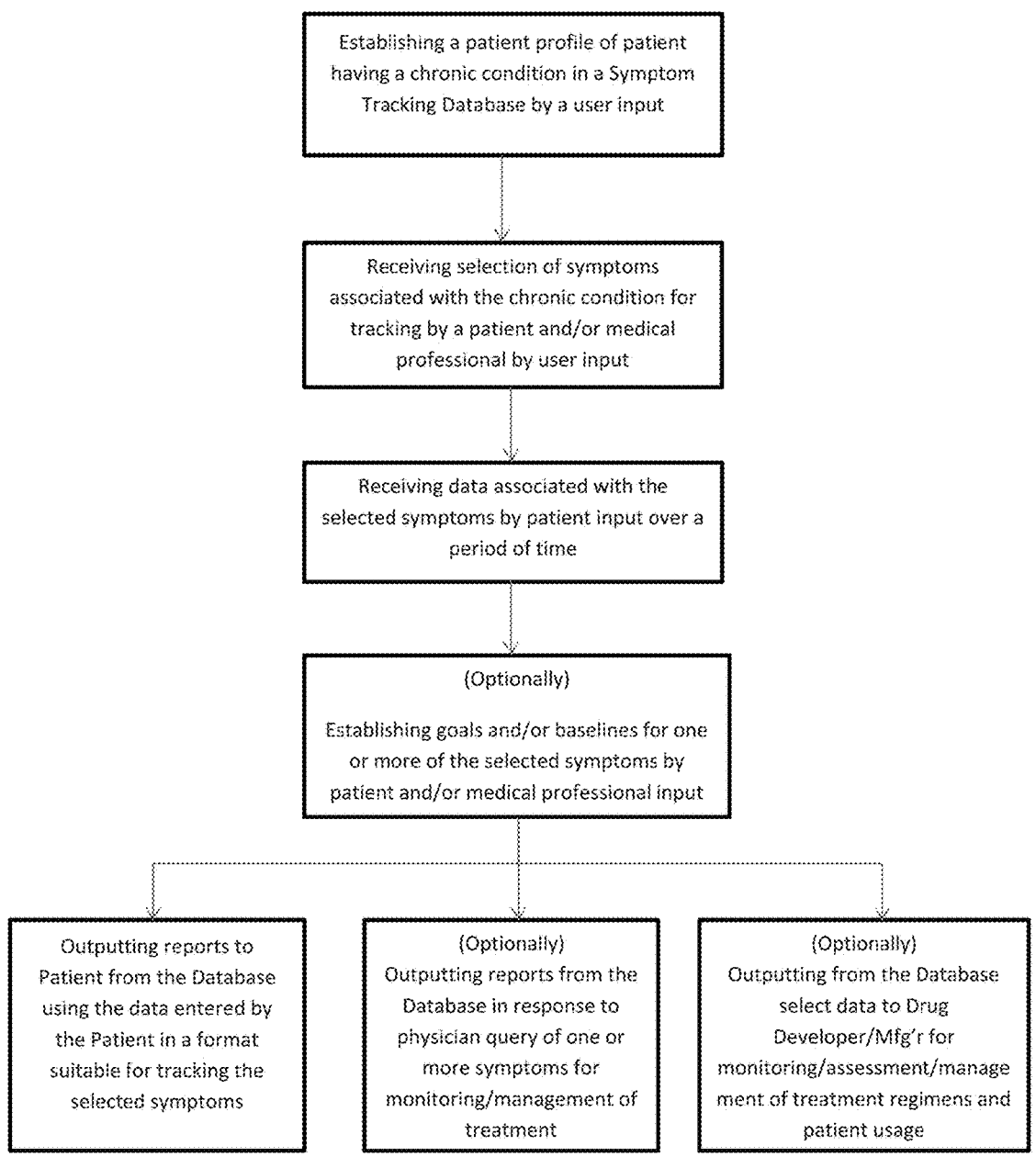
FIG. 13 illustrates an example method using a symptom tracking system in accordance with embodiments of the invention.

FIGS. 13-18 describe various methods by which a chronic condition or associated treatment can be managed or by which production/dissemination of drug information can be managed. FIG. 13 describes a method of management treatment including: establishing a patient profile of a patient having a chronic condition in a symptom tracking database by a user input; receiving selection of symptoms associated with the chronic condition for tracking by a patient and/or medical professional by user input; receiving data associated with the selected symptoms by the patient input over a period of time; optionally, establishing goals and/or baselines for one or more of the selected symptoms by patient and/or medical professional input; outputting reports to patient from the database using the data entered by the patient in a format suitable for tracking the selected symptoms; optionally, outputting reports from the database in response to physician query of one or more symptoms for monitoring or management of treatment; and optionally, outputting from the database select data to a drug developer or drug manufacturer for monitoring, assessment, or management of treatment regimens and patient usage.

Figure 14:
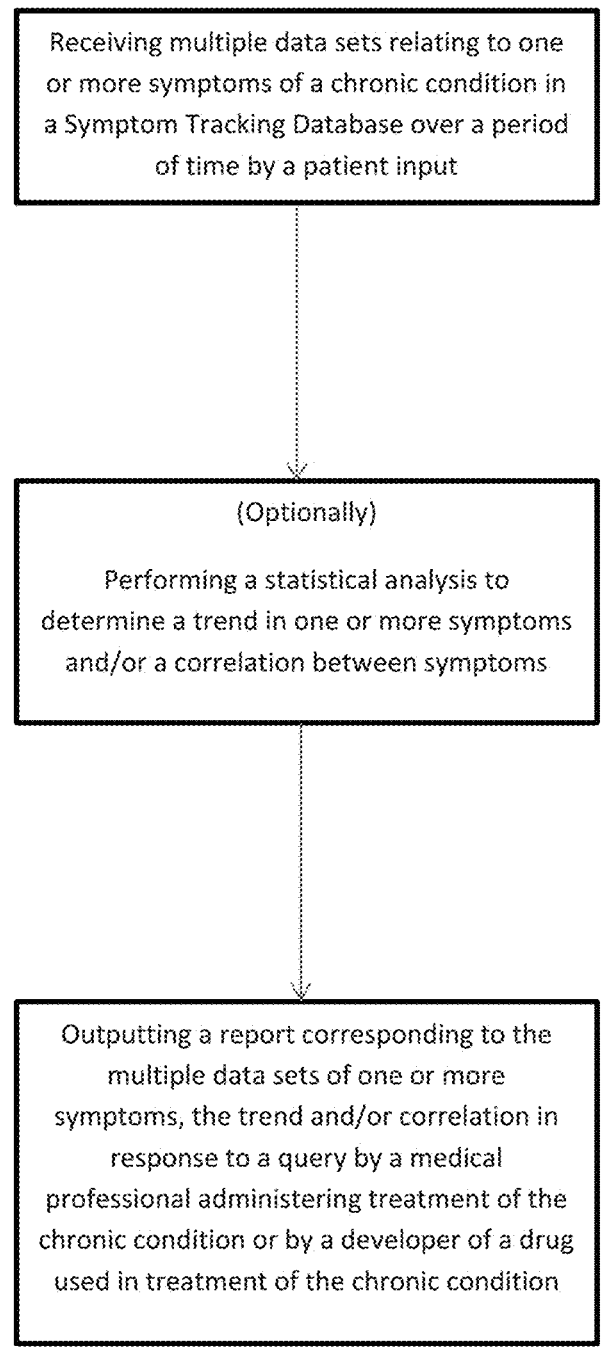
FIG. 14 illustrates an example method using a symptom tracking system in accordance with embodiments of the invention.

FIG. 14 describes a method of treatment management including steps of: receiving multiple data sets relating to one or more symptoms of a chronic condition in a symptom tracking information system over a period of time by a patient input; optionally, performing a statistical analysis to determine a trend in one or more symptoms and/or a correlation between symptoms; and outputting a report corresponding to the multiple data sets of one or more symptoms, the trend and/or correlation in response to a query by a medical professional administering treatment of the chronic condition or by a developer of a drug used in treatment of the chronic condition.

Figure 15:
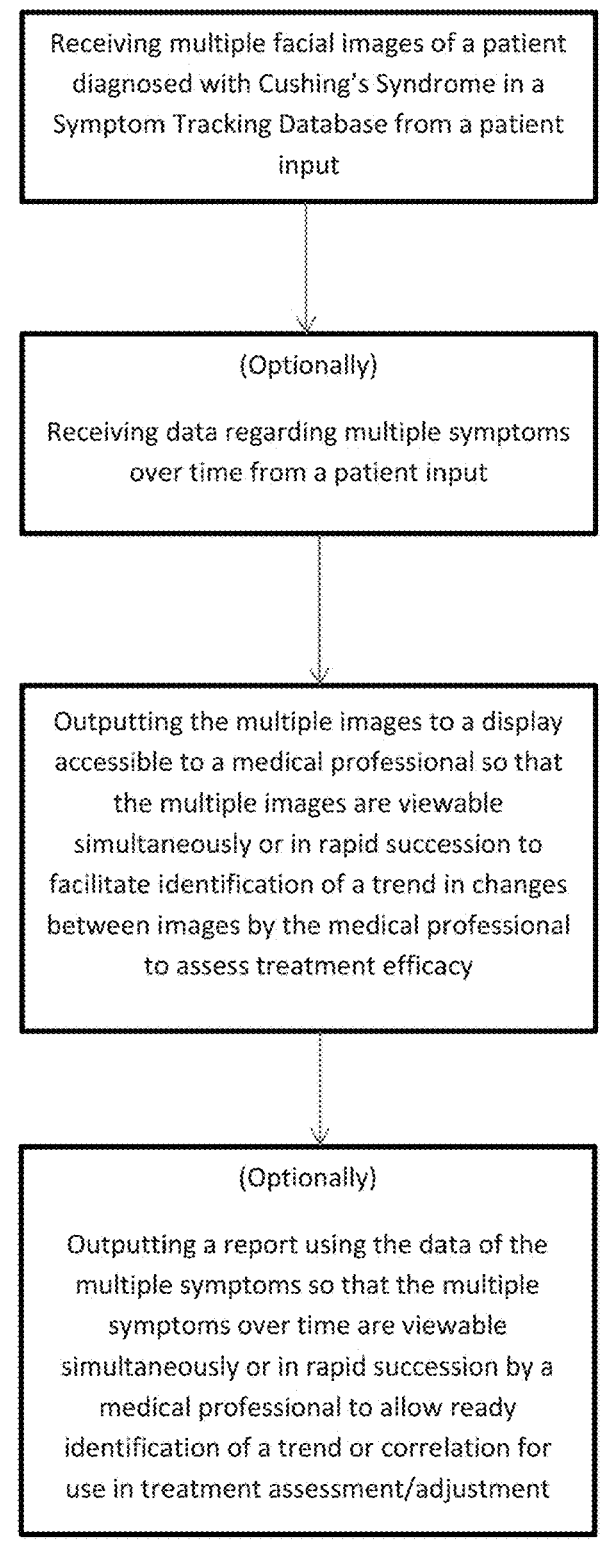
FIG. 15 illustrates an example method using a symptom tracking system in accordance with embodiments of the invention.

FIG. 15 describes a method of treatment management including steps of: receiving multiple facial images of a patient diagnosed with Cushing's Syndrome in a symptom tracking information system from a patient input; optionally, receiving data regarding multiple symptoms over time from a patient input, outputting the multiple images to a display accessible to a medical professional so that the multiple images are viewable simultaneously or in rapid succession to facilitate identification of a trend in changes between images by the medical professional to assess treatment efficacy; and optionally, outputting a report using the data of the multiple symptoms so that the multiple symptoms over time are viewable simultaneously or in rapid succession by a medical professional to allow ready identification of a trend or correlation for use in treatment assessment/adjustment. In another aspect, a method of treatment management may include steps of: receiving data regarding multiple symptoms over time from a patient input; and outputting a report using the data of the multiple symptoms so that the multiple symptoms over time are viewable simultaneously or in rapid succession by a medical professional to allow ready identification of a trend or correlation for use in treatment assessment/adjustment.

Figure 16:
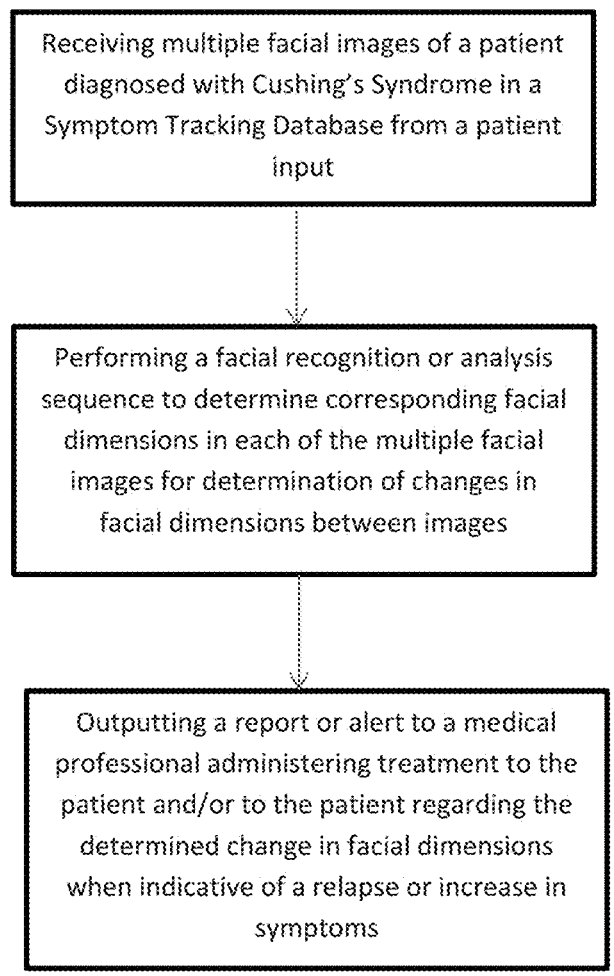
FIG. 16 illustrates an example method using a symptom tracking system in accordance with embodiments of the invention.

FIG. 16 describes a method of treatment management including steps of: receiving multiple facial images of a patient diagnosed with Cushing's Syndrome in a symptom tracking information system from a patient input; performing a facial recognition or analysis sequence to determine corresponding facial dimensions in each of the multiple facial images for determination of changes in facial dimensions between images; and outputting a report or alert to a medical professional administering treatment to the patient and/or to the patient regarding the determined change in facial dimensions when indicative of a relapse or increase in symptoms.

In certain embodiments, the system may further analyze the tracked symptoms and attributes using algorithms input by a user, medical professional, or drug developer. Such algorithms may incorporate relationship or information obtained through clinical studies or may relate to various other concerns, such as various drug supply or administrative processes. Examples of information that may be utilized within such systems include drug information relating to the drug treatment of concern. For example, studies indicate that in administration of mifepristone, plasma levels within the patient drives the drug response. By including this relationship within an algorithm of the system, the system may identify attributes, symptoms, or combinations thereof that correspond with insufficient plasma levels. Such factors may relate to insufficient titration, low dosages, patient attributes, age, diet, through various interactions that may be undetermined. Utilizing the system to store, relate and analyze such factors, however, allows a user to monitor and track various factors and symptoms and intervene as needed to ensure appropriate plasma levels are maintained and facilitate optimized treatment outcomes. Advantageously, the system may provide these benefits even without identifying the relationship to plasma levels or that the plasma level was the factor at issue. This relationship demonstrates some of the complexities and challenges associated with managing treatment of a chronic condition utilizing administration of a drug, particularly in vulnerable patient sub-populations.

Patients utilizing mifepristone to treat medical conditions require intensive follow-up to achieve optimal care and resolution of symptoms, which can lead to variable patient outcomes. Patients in which symptom tracking may be used to improve treatment can be difficult to identify before treatment is either discontinued by the patient or by the physician. For various reasons, such as poor patient compliance, reduced response to prescribed treatment, or influence of external aggravating factors, symptoms may worsen or frequent relapses may occur leading to discontinued treatment. By tracking patient symptoms, the methods described herein allows the physician, as well as the patient, to take a more active role treatment before relapse occurs, which may in turn, improve patient compliance, treatment efficacy and assist in identifying aggravating factors before significant worsening of symptoms occurs.

In some embodiments, the system may utilize any number of algorithms to determine statistical relevance of one or more attributes and symptoms to a result, the result being associated with a relapse. By applying statistical analysis, the system can determine that a relationship is caused by something other than mere random chance so as to determine if the field of information or combination of fields is statistically significant to the desired result. The analysis provides a "p-value" representing the probability that the results is attributable to random chance. In general, a 5% or lower p-value is considered to be statistically significant, although the threshold of significance and desired confidence level may be selected or varied as desired to facilitate a desired result or preventing a relapse or improve treatment approaches.

In some embodiments, the system may utilize an algorithm that applies a known or predicted association between one or more fields and a result that is input by a user or included in a system update. Such algorithms may be determined periodically as associations are identified through clinical studies or otherwise. In some embodiments, the system may apply statistical analysis to determine associations between one or more fields and a result in addition to applying an algorithm input into the system such that the statistical analysis of various fields of information can be reassessed as various other associations are identified over time. These features provide further improvements as ever more complex interactions between the fields of information can be identified and alerts or reports outputted as need to inhibit or reduce adverse effects associated with such interactions and prevent relapse.

While much has been described with respect to analysis and output of data in regard to a particular patient for management of individual patients, these and similar aspects described above may also be applied to collection of symptom data in regard to patient populations, which is particularly advantageous for managing treatment regimens by patient population, which includes various administrative considerations. For example, the symptom tracking system may analyze symptom information from various populations to project or predict a response or to project when a patient may be having a recurrence. In one example regarding response to medication: by breaking patients into a dosing cohort (1 tablet/day to 4 tablets per day), one could then see rate of change in symptoms of themselves versus their and other cohorts, which can be an important tool to the physician in managing treatment. In another aspect, one could also see how nearly all aspects discussed herein here could be compared with others. Anytime one calculates a slope (change in a symptom/measure over time) in regard to an attribute, factor or symptoms, then one could break the information into cohorts, to compare and provide evidence/information to physicians and patients. These aspects would be useful to manage treatment of patient communities by determining a subset of specific cohorts where patients are in disease progression.

While the examples described above are illustrative of some of the basic concepts described herein, it is appreciated that these advantages extend to risk factors and interactions between risk factors that are far more complex, which conventional treatment methods fail to recognize or address and might otherwise prevent a number of patients from receiving optimal treatment. The above described embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A method of managing treatment of a chronic condition or disorder associated with an outwardly visible facial symptom in a patient, the method comprising:
    measuring a plurality of physiological parameters including facial parameters, said measuring including obtaining a plurality of patient facial images over a period of time, wherein said plurality of facial images are obtained by the patient at about the same time of day at regular intervals over said period of time;
    wherein said plurality of patient facial images comprises:
    i. a baseline patient facial image obtained at a first time of day on a baseline day and including at least one measurement of a facial dimension that remains constant and at least one measurement of a facial dimension of a changeable portion of the face, and
    ii. a subsequent patient facial image obtained subsequently during the period of time at about said first time of day on a day subsequent to said baseline day during the period of time, and including at least one measurement of a facial dimension of a changeable portion of the face,
    wherein said at least one facial dimension measurement comprises determining a distance between an eye and another facial feature;
    receiving said patient facial images and facial dimension measurements in a symptom tracking system comprising a processor and an information management system,
    comparing a subsequent patient facial dimension measurement to the baseline patient facial dimension measurement using said processor;
    calculating, with the system, a slope using the processor by dividing the change between two of said facial dimension measurements from the plurality of facial images;
    determining a change or trend of change of a facial dimension based on the calculated slope and outputting a report tracking the patient facial dimension measurements and/or the determined change or trend of change.

2. The method of claim 1, wherein the chronic condition comprises an endocrine disorder, and the method further comprising receiving additional physiological measurements regarding one or more of weight, fat pad thickness, body composition, skin discoloration, and blood pressure.

3. The method of claim 2, further comprising receiving one or more patient attributes, and wherein the report comprises displaying information based on the received patient facial images and facial dimension measurements in conjunction with said one or more patient attributes.

4. The method of claim 3, wherein said one or more patient attributes is selected from patient age, sex, location, duration of treatment, date of diagnosis, and treatment regimen.

5. The method of claim 3, wherein the report comprises test result information regarding a compound in the patient's blood.

6. The method of claim 1, wherein receiving said patient facial images and facial dimension measurements comprises receiving said patient facial images and facial dimension measurements from a plurality of patients the method further comprising:
breaking the data from the plurality of patients into cohorts; and
reporting information relating to a particular cohort to the physician(s) and/or the patient(s) to improve management of treatment.

7. The method of claim 6, further comprising:
analyzing the said patient facial images and facial dimension measurements from the plurality of patients, using the processor, to determine a community trend in a particular patient community, the patient community being a subset of patients of the plurality of patients that are identified as being in disease progression based on the patient facial images and facial dimension measurements received from the plurality of patients;
wherein the report comprises information relating to a community trend.

8. The method of claim 1, further comprising receiving a test result selected from a physiological measurement and compound testing for a compound in the patient's blood selected from glucose, cortisol, ACTH, FKBP51 mRNA, and FKBP51.

9. The method of claim 1, wherein the chronic condition comprises Cushing's Syndrome, and managing treatment comprises administration of mifepristone.

10. The method of claim 1, further comprising:
receiving, with the system, one or more physiological measurements including any of: weight, blood pressure and waist size of the patient, wherein the one or more physiological measurements are obtained by the patient at the regular intervals at about the same time of day;
wherein the course of treatment is further determined based on the one or more physiological measurements.

11. The method of claim 1, further comprising:
receiving, with the system, one or more subjective attributes of the patient including any of: a physical state and an emotional state, wherein the one or more subjective attributes are obtained by the patient at the regular intervals at about the same time of day;
wherein the course of treatment is further determined based on the one or more subjective attributes.

12. A method for managing the treatment of a chronic disease or disorder associated with an outwardly visible facial symptom in a patient, comprising:
measuring a plurality of physiological parameters including facial parameters, said measuring including obtaining a plurality of patient facial images over a period of time, wherein said plurality of facial images are obtained by the patient at about the same time of day at regular intervals over said period of time, wherein said measuring comprises:
receiving a first facial image of the patient on a server comprising a processor, wherein said first image is captured at a first time on a first day during the period of time;
measuring, from said first facial image using said processor, at least one facial dimension that remains constant, and at least one facial dimension of a changeable portion of the face, wherein each of said measuring of at least one facial dimension comprises determining a distance between an eye and another facial feature;
receiving a second facial image of the patient on said server, wherein said second facial image is captured on a second day subsequent to said first day at about the same time as the first time;
measuring, from said second facial image using the processor, said at least one facial dimension of a changeable portion of the face wherein said measuring of at least one facial dimension comprises determining a distance between an eye and another facial feature;
receiving said patient facial images and facial dimension measurements in a symptom tracking system in communication with the server,
comparing the at least one facial dimension measurement of the changeable portion of the face obtained from each of the first image and the second image using a processor to determine a change in the outwardly visible facial symptom;
calculating a slope using the processor by dividing the change by the duration of time between said facial dimension measurements; and
determining a change or trend of change of a facial dimension based on the calculated slope.

13. The method of claim 12, wherein the server is accessible online such that the first facial image and the second facial image are uploaded by the patient to the server and assigning a task to the intended recipient.

14. The method of claim 12, further comprising:
receiving a plurality of facial images including the first and second facial images, the plurality of facial images being captured sequentially over the period of time at about the same time of day; and
comparing the plurality of facial images using said processor to determine a trend associated with the change in the outwardly visible facial symptom, wherein a course of treatment is determined in response to the determined trend in the outwardly visible facial symptom.

15. The method of claim 12, wherein the outwardly visible facial symptom is selected from a facial size and a facial shape.

16. The method of claim 15, wherein the chronic disease or disorder is Cushing's Syndrome, and managing treatment comprises administration of mifepristone.

17. A system for managing the treatment of a chronic disease or disorder associated with an outwardly visible facial symptom in a patient, the system comprising:
- one or more image capture devices adapted for capturing a plurality of facial images of the patient sequentially during a monitoring period, said plurality of facial images consisting of a first facial image and one or more subsequent facial images;
- a server configured for receiving and storing the plurality of facial images of the patient in an information system; and
- a processor communicatively coupled with the server and having instructions recorded on a non-transitory recording medium, the instruction being configured for:
- measuring a plurality of physiological parameters including facial parameters, said measuring including obtaining a plurality of patient facial images over a period of time, wherein said plurality of facial images are obtained by the patient at about the same time of day at regular intervals over said period of time;
- measuring, from a facial image, a facial dimension that remains constant, and a facial dimension of a changeable portion of a face, wherein each measuring of a facial dimension comprises determining a distance between an eye and another facial feature;
- calculating a slope by dividing the change between said facial dimension measurements of at least two facial images of the plurality by the duration of time between said measurements of the two facial images of the plurality;
- comparing the facial dimension measurements, slopes, or both, from the at least two facial images of the plurality of facial images of the patient to determine a change or a trend of change of a facial dimension; and
- determining a change or trend of change of a facial dimension based on the calculated slope.

18. The system of claim 17, further comprising:
- a patient input for receiving the plurality of facial images obtained by the one or more image capture devices from the patient; and
- a physician input for receiving patient treatment information used in determining the course of treatment.

19. The system of claim 17, wherein the server is accessible online such that the plurality of facial images are uploadable by the patient through the Internet and the plurality of facial images are accessible by the physician through the Internet.

20. A method for managing the treatment of a chronic disease or disorder associated with an outwardly visible facial symptom in a patient, the method comprising:
- measuring a plurality of physiological parameters including facial parameters, said measuring including obtaining a plurality of patient facial images over a period of time, wherein said plurality of facial images are obtained by the patient at about the same time of day at regular intervals over said period of time;
- obtaining said patient facial images and facial dimension measurements in a symptom tracking system using a processor,
- and wherein said obtaining comprises:
  a) obtaining, from said first facial image, at least one measurement of a facial dimension that remains constant, and at least one measurement of a facial dimension of a changeable portion of the face; and
  b) obtaining, from each subsequent patient facial image, at least one measurement of a facial dimension of a changeable portion of the face,
- wherein each facial dimension measurement comprises determining a distance between an eye and another facial feature;
- comparing a first patient facial dimension measurement of a first facial image of the plurality to a subsequent patient facial dimension measurement of a subsequent patient facial image using said processor;
- calculating, with the system, a slope using the processor by dividing a change between the facial dimension measurements from the first and subsequent facial image to determine a change or trend of change of a facial dimension based on the calculated slope;
- outputting using the processor the multiple facial images to a display accessible to a medical professional so that the multiple facial images are viewable simultaneously or in rapid succession to facilitate identification of a trend in changes between facial images by the medical professional to assess treatment efficacy; and
- determining a change or trend of change of a facial dimension based on the calculated slope.

21. The of claim 20, further comprising:
- receiving the plurality of facial images regarding multiple outwardly visible facial symptoms over time from a patient input; and
- outputting a report using the plurality of facial images and the facial dimension measurements of the multiple outwardly visible facial symptoms so that the multiple outwardly visible facial symptoms over time are viewable simultaneously or in rapid succession by a medical professional to allow ready identification of the trend or correlation for use in treatment assessment, treatment adjustment, or both treatment assessment and treatment adjustment.

22. The method of claim 21, further comprising:
- outputting a report or alert to a medical professional administering treatment to the patient and/or to the patient regarding the determined change in facial dimensions when indicative of a relapse of said chronic disease or disorder, or of an increase in a facial dimension in one or more outwardly visible facial symptoms.

23. The method of claim 21, wherein the chronic disease or disorder comprises an endocrine disorder and wherein managing treatment comprising modifying a drug regimen.

24. The method of claim 20 wherein the chronic disease or disorder comprises Cushing's Syndrome, and wherein managing treatment comprises administering mifepristone.

* * * * *